United States Patent
Yukawa et al.

(10) Patent No.: US 12,305,199 B2
(45) Date of Patent: May 20, 2025

(54) **RECOMBINANT OF *HYDROGENOPHILUS* BACTERIUM PRODUCING LACTIC ACID**

(71) Applicant: Utilization of Carbon Dioxide Institute Co., Ltd., Tokyo (JP)

(72) Inventors: Hideaki Yukawa, Tokyo (JP); Naoto Ohtani, Tokyo (JP)

(73) Assignee: Utilization of Carbon Dioxide Institute Co., Ltd., Tokyo (JP)

( * ) Notice: Subject to any disclaimer, the term of this patent is extended or adjusted under 35 U.S.C. 154(b) by 549 days.

(21) Appl. No.: 17/631,066

(22) PCT Filed: Aug. 9, 2019

(86) PCT No.: PCT/JP2019/031741
§ 371 (c)(1),
(2) Date: Jan. 28, 2022

(87) PCT Pub. No.: WO2021/028993
PCT Pub. Date: Feb. 18, 2021

(65) Prior Publication Data
US 2022/0290109 A1    Sep. 15, 2022

(51) Int. Cl.
*C12N 9/04* (2006.01)
*C12P 7/56* (2006.01)

(52) U.S. Cl.
CPC .............. *C12N 9/0006* (2013.01); *C12P 7/56* (2013.01); *C12Y 101/01027* (2013.01); *C12Y 101/01037* (2013.01)

(58) Field of Classification Search
CPC ......... C12N 9/0006; C12N 1/205; C12P 7/56; C12Y 101/01027; C12Y 101/01037; C12R 2001/01
See application file for complete search history.

(56) References Cited

U.S. PATENT DOCUMENTS

| | | | |
|---|---|---|---|
| 2015/0232895 A1 | 8/2015 | Hara et al. | |
| 2021/0324427 A1* | 10/2021 | Boisart | .......... C12Y 101/01028 |
| 2021/0403928 A1* | 12/2021 | Hideaki | .................... C12P 7/56 |

FOREIGN PATENT DOCUMENTS

| | | |
|---|---|---|
| JP | 2014-183743 A | 10/2014 |
| JP | 2015-023854 A | 2/2015 |
| JP | 2017-093465 A | 6/2017 |
| WO | 03/102152 A2 | 12/2003 |
| WO | 2016/012296 A1 | 1/2016 |

OTHER PUBLICATIONS

Banerjee et al., Improving enzymes for biomass conversion: A basic research perspective. Bioenerg. Res., 2010, vol. 3: 82-92. (Year: 2010).*

Branduardi et al., Lactate production yield from engineered yeasts is dependent fromthe host background, the lactate dehydrogenase source and the lactate export. Microbial cell Factories., 2006, vol. 5:4, pp. 1-12. (Year: 2006).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Goto et al., "Growth and Taxonomy of Thermophilic Hydrogen Bacteria," Agricultural and Biological Chemistry, 42 (7): 1305-1308 (1978).
Chang et al., "Homofermentative Production of D- or L-Lactate in Metabolically Engineered *Escherichia coli* RR1," Applied and Environmental Microbiology, 65 (4): 1384-1389 (1999).
Angermayr et al., "Engineering a Cyanobacterial Cell Factory for Production of Lactic Acid," Applied and Environmental Microbiology, 78 (19): 7098-7106 (2012).
Chai et al., "A Widely Conserved Gene Cluster Required for Lactate Utilization in Bacillus subtilis and Its Involvement In Biofilm Formation," Journal of Bacteriology, 191 (8): 2423-2430 (2009).

(Continued)

*Primary Examiner* — Ganapathirama Raghu
(74) *Attorney, Agent, or Firm* — Morgan, Lewis & Bockius LLP

(57) ABSTRACT

When lactate dehydrogenase gene and/or malate/lactate dehydrogenase gene is/are introduced into a *Hydrogenophilus* bacterium as well as one or more of the three lactic acid-utilizing enzyme genes on the genome of the *Hydrogenophilus* bacterium is/are disrupted, lactic acid-producing ability is remarkably increased. The inventors of the present invention have identified the three lactic acid-utilizing enzyme genes of the *Hydrogenophilus* bacterium. When lactate permease gene is further introduced into the recombinant, lactic acid-producing ability is further increased. The recombinant of the present invention effectively produces lactic acid using carbon dioxide as a sole carbon source, and therefore, it is able to efficiently produce the material of biodegradable plastics, while solving global warming caused by increased emissions of carbon dioxide.

17 Claims, 1 Drawing Sheet
Specification includes a Sequence Listing.

(56) References Cited

OTHER PUBLICATIONS

Shigetomi, "A Study of CO2 Fixation Utilizing Microorganisms," Journal of Mitsubishi Research Institute No. 34 (1999) (see partial English translation).

Pinchuk et al., "Genomic reconstruction of Shewanella oneidensis MR-1 metabolism reveals a previously uncharacterized machinery for lactate utilization," PNAS, 106 (8): 2874-2879 (2009).

Orlygsson et al., "The Family Hydrogenophilacaea," in Rosenberg, The Prokaryotes-Alphaproteobacteria and Betaproteobacteria (2014).

International Search Report issued in corresponding International Patent Application No. PCT/JP2019/031741 dated Oct. 29, 2019.

Extended European Search Report issued in corresponding European Patent Application No. 19941249.5 dated Jul. 19, 2022.

Research Report of Public Interest Incorporated Foundation Iwatani Naozi Kinen Zaidan, 41: 57-59 (2018) (see partial English translation).

Hayashi et al., "*Hydrogenophilus thermoluteolus* gen. nov., sp. nov., a thermophilic, facultatively chemolithoautotrophic, hydrogen-oxidizing bacterium," International Journal of Systematic Bacteriology, 49: 783-786 (1999).

Uniport Database A0A2Z6DZH7 (2018).

Hwang et al., "LUD, a new protein domain associated with lactate utilization," BMC Bioinformatics, 14: 341 (2013).

Ishii et al., "Trasciptome profiles of central carbon metabolism under autotrophic, heterotrophic, and mixotrophic conditions in Hydrogenophilus thermoluteolus TH-1," Journal of Japanese Society for Extremophiles, 16: 27-36 (2017).

\* cited by examiner

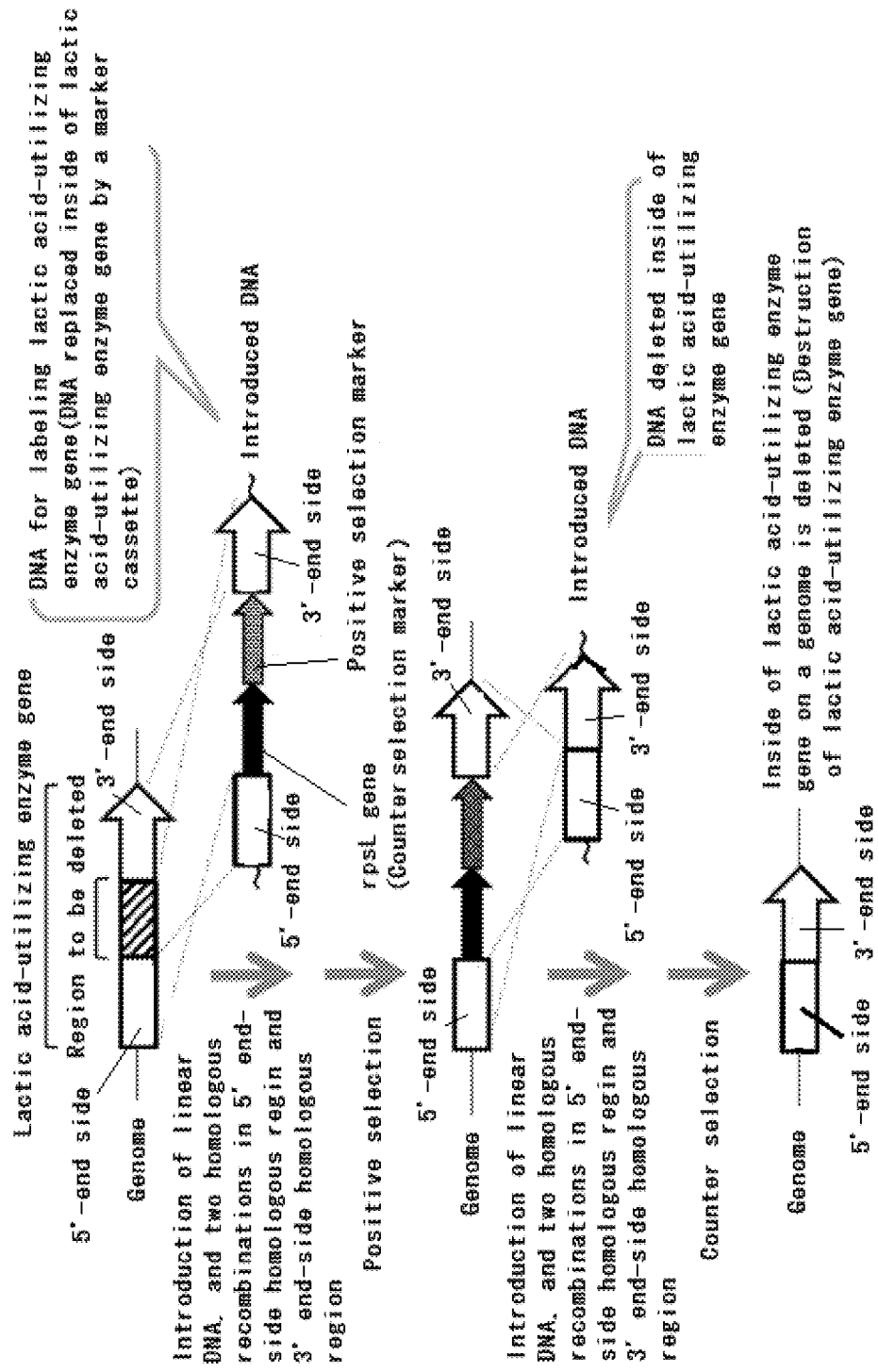

RECOMBINANT OF *HYDROGENOPHILUS* BACTERIUM PRODUCING LACTIC ACID

Sequence Listing Submission via EFS-Web

A computer readable text file, entitled "SequenceListing.txt," created on Jan. 11, 2022 with a file size of 54,903 bytes contains the sequence listing for this application and is hereby incorporated by reference in its entirety.

TECHNICAL FIELD

The present invention relates to a recombinant *Hydrogenophilus* bacterium harboring the ability to produce lactic acid, and to a method for producing lactic acid using the same.

BACKGROUND ART

The Paris Agreement, which was adopted in 2015, provides that global emissions of greenhouse gases should be promptly reduced. Under the Agreement, Japan set the goal of reducing her emission of greenhouse gases such as carbon dioxide and methane by 26% compared with year 2013 levels, by the year 2030.

Worldwide, the majority of the production of chemicals depends on petroleum resources, exacerbating the problem of increased greenhouse gas emissions. Accordingly, departure from petroleum dependency is a desirable strategy for the production of chemicals, and research and development of biorefineries that produce green chemicals from biomass is being earnestly carried out in various countries. However, the saccharification of biomass for use as raw materials of microbial fermentation necessitates complex processes, beside being costly.

As part of research geared towards departure from petroleum dependency, gases such as carbon dioxide, methane, and carbon monoxide have attracted attention as more sustainable carbon sources, and techniques for producing valuable chemicals and biofuels using microorganisms that utilize these gases are the subject of intense interest. In particular, carbon fixation of carbon dioxide and efficient utilization of carbon dioxide, a significant contributor to global warming, is highly anticipated.

Biodegradable plastics, which are eventually decomposed to water and carbon dioxide by microorganisms in nature, have attracted attention in light of the problems of sea pollution by plastic garbage, etc. Biodegradable plastics are categorized into bacterial products series, natural products series and chemical synthetic series according to method of manufacture. Polylactic acid (lactic acid resin), of which research and practical realization has proceeded the fastest of all biodegradable plastics, is regarded as an intermediate biodegradable plastic between bacterial products series and chemical synthetic series since its raw material is lactic acid, a product of the glycolysis system, an intravital metabolic pathway. That is, polylactic acid is produced by the purification of lactic acid produced by microbial fermentation and chemical polycondensation. Current polylactic acid production uses biomass as a raw material, the conversion of biomass into saccharides requires complicated steps, as aforementioned, and therefore, current polylactic acid production has a problem of a high cost.

Accordingly, a practicable method which is able to produce lactic acid in simpler steps is required. In particular, a practicable method which is able to produce lactic acid by carbon dioxide fixation.

Lactic acid is produced from pyruvic acid, intravital important metabolic product. That is, lactic acid is produced from pyruvic acid by catalytic activity of lactate dehydrogenase.

As a technology which manufactures lactic acid using a recombinant microorganism, Patent Literature 1 describes a method for producing lactic acid using a transformant obtained by introducing the lactate dehydrogenase gene (ldh gene) of *Lactobacillus helvetics* or *Bacillus megaterium* into a yeast strain.

Patent Literature 2 describes a method for producing lactic acid using a transformant obtained by introducing *Lactobacillus pentosus* LDH gene as a lactate dehydrogenase gene into *Schizosaccharomyces pombe*.

Patent Literature 3 describes a method for producing lactic acid using a transformant obtained by introducing *Thermoanaerobacter pseudethanolicus* ldh gene as a lactate dehydrogenase gene into *Moorella thermoacetica*.

Patent Literature 4 describes a method for producing lactic acid using a transformant obtained by introducing *Lactobacillus delbrueckii* hdhD gene or ldhA gene as a lactate dehydrogenase gene into *Geobacillus thermoglucosidans*.

Non Patent Literature 1 describes a method for producing lactic acid using a transformant obtained by introducing the lactate dehydrogenase gene of *Lactobacillus casei* into *Escherichia coli*.

However, all these methods are methods for producing lactic acid using sugar as a carbon source, and not methods for producing lactic acid using carbon dioxide as a carbon source.

Non Patent Literature 2 describes a method for producing lactic acid using a transformant obtained by introducing the lactate dehydrogenase gene of *Bacillus subtilis* into *Synechocystis* sp. PCC6803 strain. This method is for producing lactic acid using Cyanobacterium, which is a photosynthetic bacterium, as a host and using sodium hydrogen carbonate as a carbon source.

Cyanobacteria have a higher carbon fixation ability of carbon dioxide as compared to that of plants. However, the method of using Cyanobacterium as a host has not been put into practical use as an industrial method for producing lactic acid since carbon dioxide fixation ability of Cyanobacteria is insufficient.

Patent Literature 5 describes a method for producing lactic acid using a transformant obtained by introducing *Thermus thermophilus* ldh gene as a lactate dehydrogenase gene into *Hydrogenobacter thermophilus*.

*Hydrogenobacter thermophilus* is a hydrogen oxidizing bacterium which grows twofold in 1.5 hours. However, to apply current is necessary in order to produce sufficient amounts of lactic acid, and therefore, the method using *Hydrogenobacter thermophilus* as a host has not been put into practical use as an industrial method for producing lactic acid.

CITATION LIST

Patent Literatures

[Patent Literature 1] JP2005-528106A
[Patent Literature 2] JP2014/030655A1
[Patent Literature 3] JP2015-023854A
[Patent Literature 4] JP2017-523778A
[Patent Literature 5] JP2017-093465A. Non Patent Literatures

[Non Patent Literature 1] Homofermentative production of D- or L-lactate in metabolically engineered *Escherichia coli* RR1. Chang D E, Jung H C, Rhee J S, Pan J G. Appl. Environ. Microbiol. (1999) 65:1384-1389

[Non Patent Literature 2] Engineering a cyanobacterial cell factory for production of lactic acid. Angermayr S A, Paszota M, Hellingwerf K J. Appl. Environ. Microbiol. (2012) 78:7098-7106

SUMMARY OF INVENTION

Technical Problem

The objective of the present invention is to provide a recombinant *Hydrogenophilus* bacterium that is capable of efficiently producing lactic acid utilizing carbon dioxide as a sole carbon source, and a method for efficiently producing lactic acid using this recombinant.

Solution to Problem

*Hydrogenophilus* bacteria are hydrogen oxidizing bacteria which grow by producing organic substances from carbon dioxide by utilizing hydrogen energy. The growth rate of hydrogen oxidizing bacteria is generally extremely slow, however, the growth rate of *Hydrogenophilus* bacteria is fast, and their carbon fixation ability of carbon dioxide is remarkably higher than that of plants and photosynthetic bacteria.

However, *Hydrogenophilus* bacteria do not have an ability to produce lactic acid at an industrial scale. *Hydrogenophilus* bacteria do not have a lactate dehydrogenase gene and a malate/lactate dehydrogenase gene, which are known to encode an enzyme catalyzing the reaction of producing lactic acid from pyrubic acid. In order to provide the bacteria with an ability to produce lactic acid at an industrial scale, it is desirable to introduce genes of enzymes that catalyze the reaction of producing lactic acid.

However, the research of the inventors of the present invention has revealed that when a heterologous gene is introduced into *Hydrogenophilus* bacteria using a vector that functions within the *Hydrogenophilus* bacteria, a functioning protein often is not produced or is insufficiently produced. Genes which bring about activity within bacteria other than the genus *Hydrogenophilus* often do not, or insufficiently, bring about activity within the *Hydrogenophilus* bacteria.

Faced with such a situation, the inventors of the present invention have found that when a lactate dehydrogenase gene and/or a malate/lactate dehydrogenase gene is/are introduced into *Hydrogenophilus* bacteria, the gene(s) function(s) and bring(s) about high activity within the *Hydrogenophilus* bacteria.

Further, the inventors of the present invention have found that ldh gene of *Parageobacillus thermoglucosidasius*, *Geobacillus kaustophilus* or *Thermus thermophilus* of the lactate dehydrogenase genes and mldh gene of *Thermus thermophilus* and mldh-1 and mldh-2 genes of *Meiothermus ruber* of the malate/lactate dehydrogenase genes bring about higher enzymatic activity expression especially in *Hydrogenophilus* bacteria.

The *Hydrogenophilus* bacterium is known to utilize lactic acid (Agric. Biol. Chem. (1978) 42(7): 1305-1308; Orlygsson J, Kristjansson J. K. (2014) The Family Hydrogenophilaceae. In: Rosenberg E., DeLong E. F., Lory S., Stackebrandt E., Thompson F. (eds) The Prokaryotes. Springer, Berlin, Heidelberg).

The inventors of the present invention postulated that HPTL_1694, HPTL_1695, and HPTL_1696 genes, which appear side by side on the genome of *Hydrogenophilus thermoluteolus*, function as lactic acid-utilizing enzyme genes.

It is conceivable that, when a lactic acid-utilizing enzyme gene functions, lactic acid produced inside the cells of the *Hydrogenophilus* bacterium is utilized, and the amount of lactic acid secreted into a medium supernatant is therefore reduced.

The inventors of the present invention have observed that, when one or more genes out of HPTL_1694, HPTL_1695, and HPTL_1696 on the genome is/are disrupted in a *Hydrogenophilus thermoluteolus* transformant having the lactate dehydrogenase gene and/or the malate/lactate dehydrogenase gene introduced thereinto, the amount of lactic acid secreted into the medium is markedly increased. In view of this, the inventors concluded that HPTL_1694, HPTL_1695, and HPTL_1696 genes are lactic acid-utilizing enzyme genes.

The disruption of any one or more of HPTL_1694, HPTL_1695, and HPTL_1696 genes enhanced lactic acid-producing ability of the resultant cells, and hence it is conceivable that these three genes form an operon, and that the three proteins encoded by these genes form a complex that exhibits the function of utilizing lactic acid.

The inventors of the present invention have also observed that the above-mentioned lactic acid-utilizing enzyme gene-disrupted strain extremely efficiently produces lactic acid through use of carbon dioxide as a sole carbon source.

The inventors of the present invention have also observed that, when a gene encoding a lactate permease, which promotes the secretion of lactic acid to the outside of cells, is introduced into the lactic acid-utilizing enzyme gene-disrupted strain of the *Hydrogenophilus* bacterium having the lactate dehydrogenase gene and/or the malate/lactate dehydrogenase gene introduced thereinto, the amount of lactic acid secreted into the medium is further increased.

The present invention has been completed on the basis of the above-mentioned observations, and provides the following items [1] to [8].

[1] A recombinant *Hydrogenophilus* bacterium, which has a lactate dehydrogenase gene and/or a malate/lactate dehydrogenase gene introduced thereinto, and in which one or more of three lactic acid-utilizing enzyme genes on a genome are disrupted.

[2] The recombinant *Hydrogenophilus* bacterium according to Item [1], wherein the three lactic acid-utilizing enzyme genes are formed of DNA of any one of the following (a1) to (a6), DNA of any one of the following (b1) to (b6), and DNA of any one of the following (c1) to (c6), respectively:

(a1) DNA formed of a base sequence set forth in SEQ ID NO: 1;

(a2) DNA that is formed of a base sequence having 90% or more identity to the base sequence set forth in SEQ ID NO: 1, and that encodes a polypeptide having lactic acid-utilizing enzyme activity;

(a3) DNA that hybridizes with DNA formed of a base sequence complementary to SEQ ID NO: 1 under stringent conditions, and that encodes a polypeptide having lactic acid-utilizing enzyme activity;

(a4) DNA encoding a polypeptide formed of an amino acid sequence set forth in SEQ ID NO: 2;

(a5) DNA encoding a polypeptide that is formed of an amino acid sequence having 90% or more identity to SEQ ID NO: 2, and that has lactic acid-utilizing enzyme activity; and (a6) DNA encoding a polypeptide that is formed of an amino acid sequence having one or a plurality of amino acids deleted, substituted, or added in the amino acid sequence set forth in SEQ ID NO: 2, and that has lactic acid-utilizing enzyme activity;

(b1) DNA formed of a base sequence set forth in SEQ ID NO: 3;

(b2) DNA that is formed of a base sequence having 90% or more identity to the base sequence set forth in SEQ ID NO: 3, and that encodes a polypeptide having lactic acid-utilizing enzyme activity;

(b3) DNA that hybridizes with DNA formed of a base sequence complementary to SEQ ID NO: 3 under stringent conditions, and that encodes a polypeptide having lactic acid-utilizing enzyme activity;

(b4) DNA encoding a polypeptide formed of an amino acid sequence set forth in SEQ ID NO: 4;

(b5) DNA encoding a polypeptide that is formed of an amino acid sequence having 90% or more identity to SEQ ID NO: 4, and that has lactic acid-utilizing enzyme activity; and (b6) DNA encoding a polypeptide that is formed of an amino acid sequence having one or a plurality of amino acids deleted, substituted, or added in the amino acid sequence set forth in SEQ ID NO: 4, and that has lactic acid-utilizing enzyme activity; and (c1) DNA formed of a base sequence set forth in SEQ ID NO: 5;

(c2) DNA that is formed of a base sequence having 90% or more identity to the base sequence set forth in SEQ ID NO: 5, and that encodes a polypeptide having lactic acid-utilizing enzyme activity;

(c3) DNA that hybridizes with DNA formed of a base sequence complementary to SEQ ID NO: 5 under stringent conditions, and that encodes a polypeptide having lactic acid-utilizing enzyme activity;

(c4) DNA encoding a polypeptide formed of an amino acid sequence set forth in SEQ ID NO: 6;

(c5) DNA encoding a polypeptide that is formed of an amino acid sequence having 90% or more identity to SEQ ID NO: 6, and that has lactic acid-utilizing enzyme activity; and (c6) DNA encoding a polypeptide that is formed of an amino acid sequence having one or a plurality of amino acids deleted, substituted, or added in the amino acid sequence set forth in SEQ ID NO: 6, and that has lactic acid-utilizing enzyme activity.

[3] The recombinant *Hydrogenophilus* bacterium according to Item [1] or [2], wherein the one or more of three lactic acid-utilizing enzyme genes are disrupted by introducing a deletion, an addition, a substitution, or a combination thereof, of one or a plurality of nucleotides into the one or more of three lactic acid-utilizing enzyme genes.

[4] The recombinant *Hydrogenophilus* bacterium according to any one of Items [1] to [3], wherein the lactate dehydrogenase gene is formed of DNA of any one of the following (d1) to (d6):

(d1) DNA formed of a base sequence set forth in SEQ ID NO: 9, 10, or 11;

(d2) DNA that is formed of a base sequence having 90% or more identity to the DNA formed of the base sequence set forth in SEQ ID NO: 9, 10, or 11, and that encodes a polypeptide having lactate dehydrogenase activity;

(d3) DNA that hybridizes with DNA formed of a base sequence complementary to SEQ ID NO: 9, 10, or 11 under stringent conditions, and that encodes a polypeptide having lactate dehydrogenase activity;

(d4) DNA encoding a polypeptide formed of an amino acid sequence set forth in SEQ ID NO: 12, 13, or 14;

(d5) DNA encoding a polypeptide that is formed of an amino acid sequence having 90% or more identity to SEQ ID NO: 12, 13, or 14, and that has lactate dehydrogenase activity; and (d6) DNA encoding a polypeptide that is formed of an amino acid sequence having one or a plurality of amino acids deleted, substituted, or added in the amino acid sequence set forth in SEQ ID NO: 12, 13, or 14, and that has lactate dehydrogenase activity.

[5] The recombinant *Hydrogenophilus* bacterium according to any one of Items [1] to [4], wherein the malate/lactate dehydrogenase gene is formed of DNA of any one of the following (e1) to (e6):

(e1) DNA formed of a base sequence set forth in SEQ ID NO: 15, 16, or 17;

(e2) DNA that is formed of a base sequence having 90% or more identity to the DNA formed of the base sequence set forth in SEQ ID NO: 15, 16, or 17, and that encodes a polypeptide having lactate dehydrogenase activity;

(e3) DNA that hybridizes with DNA formed of a base sequence complementary to SEQ ID NO: 15, 16, or 17 under stringent conditions, and that encodes a polypeptide having lactate dehydrogenase activity;

(e4) DNA encoding a polypeptide formed of an amino acid sequence set forth in SEQ ID NO: 18, 19, or 20;

(e5) DNA encoding a polypeptide that is formed of an amino acid sequence having 90% or more identity to SEQ ID NO: 18, 19, or 20, and that has lactate dehydrogenase activity; and (e6) DNA encoding a polypeptide that is formed of an amino acid sequence having one or a plurality of amino acids deleted, substituted, or added in the amino acid sequence set forth in SEQ ID NO: 18, 19, or 20, and that has lactate dehydrogenase activity.

[6] The recombinant *Hydrogenophilus* bacterium according to any one of Items [1] to [5], wherein the recombinant *Hydrogenophilus* bacterium further has a lactate permease gene introduced thereinto.

[7] The recombinant *Hydrogenophilus* bacterium according to Item [6], wherein the lactate permease gene is formed of DNA of any one of the following (f1) to (f6):

(f1) DNA formed of a base sequence set forth in SEQ ID NO: 21;

(f2) DNA that is formed of a base sequence having 90% or more identity to the DNA formed of the base sequence set forth in SEQ ID NO: 21, and that encodes a polypeptide having lactate permease activity;

(f3) DNA that hybridizes with DNA formed of a base sequence complementary to SEQ ID NO: 21 under stringent conditions, and that encodes a polypeptide having lactate permease activity;

(f4) DNA encoding a polypeptide formed of an amino acid sequence set forth in SEQ ID NO: 22;

(f5) DNA encoding a polypeptide that is formed of an amino acid sequence having 90% or more identity to SEQ ID NO: 22, and that has lactate permease activity; and (f6) DNA encoding a polypeptide that is formed of an amino acid sequence having one or a plurality of amino acids deleted, substituted, or added in the amino acid sequence set forth in SEQ ID NO: 22, and that has lactate permease activity.

[8] A method of producing lactic acid, including a step of culturing the recombinant *Hydrogenophilus* bacterium of any one of Items [1] to [7] through use of carbon dioxide as a substantially sole carbon source.

Advantageous Effects of Invention

Measures to counter the increase in atmospheric carbon dioxide entail reduction of carbon dioxide emissions and fixation of emitted carbon dioxide. In order to reduce carbon dioxide emissions, solar, wind, geothermal, and similar energies are utilized in place of fossil energy. However, the utilization of such energies is not yet extensive enough to repress the buildup of atmospheric carbon dioxide. Consequently, there is need to enhance atmospheric carbon fixation or recycling of emitted carbon dioxide.

Carbon fixation of carbon dioxide can occur physically or chemically, but fixation utilizing living cells, avails organic substances that can consequently be utilized as food, feed, and fuel. In so doing, carbon dioxide itself becomes a resource that can be directly converted into valuable chemical products. Accordingly, the twin problems of global warming due to increased atmospheric carbon dioxide and scarcity of food, feed, and fuel can be solved. Further, in-demand chemical products can be produced while suppressing global warming attributed to increased carbon dioxide emissions.

Biodegradable plastics of chemical products attract attention for their environmental benefits. Biodegradable plastics produced by fixation of carbon dioxide are decomposed to water and carbon dioxide by microorganisms in the environment. That is, biodegradable plastics are carbon-neutral, and are able to solve global warming attributed to increased carbon dioxide emissions, difficulty in securing plastic products necessary for life, and environmental problems such as sea pollution, together.

Hydrogen-oxidizing bacteria can grow by utilizing the chemical energy generated by the reaction of hydrogen with oxygen and by using carbon dioxide as a sole carbon source. Since hydrogen-oxidizing bacteria can produce chemical products from a mixture of oxygen, hydrogen, and carbon dioxide gases as raw material, the cells can efficiently assimilate carbon from carbon dioxide and be cultured in a simple culture medium. Growth of typical hydrogen-oxidizing bacteria is generally slow, but that of *Hydrogenophilus* bacteria is exceptionally high. The Journal of Mitsubishi Research Institute No.34 1999 describes *Hydrogenophilus* bacteria as follows: "Their proliferative capacity is so high that their carbon fixation ability of carbon dioxide cannot be compared with that of plants, which truly indicates the high carbon dioxide fixation ability of microorganisms".

When a heterologous gene is introduced into *Hydrogenophilus* bacteria using a vector that functions within the *Hydrogenophilus* bacteria, a functioning protein is often not produced. Under such a situation, by introducing lactate dehydrogenase gene and/or malate/lactate dehydrogenase gene into of *Hydrogenophilus* bacteria, the genes function within the *Hydrogenophilus* bacteria, and lactic acid could be efficiently produced.

When one or more of the three lactic acid-utilizing enzyme genes on the genome of the above-mentioned transformant of the *Hydrogenophilus* bacterium are disrupted, the amount of lactic acid produced into a medium can be remarkably increased.

When the lactate permease gene is further introduced into the lactic acid-utilizing enzyme gene-disrupted strain of the *Hydrogenophilus* bacterium having the lactate dehydrogenase gene and/or the malate/lactate dehydrogenase gene introduced thereinto, the lactate permease gene functions in the recombinant strain to increase the amount of lactic acid secreted into a medium. The lactic acid secretion amount-increasing effect of the introduction of the lactate permease gene is remarkably enhanced by the disruption of the lactic acid-utilizing enzyme gene(s) of the *Hydrogenophilus* bacterium serving as the host.

As described above, the *Hydrogenophilus* bacterium has a particularly excellent carbon dioxide fixation ability among organisms each having a carbon dioxide fixation ability. Accordingly, the use of the recombinant of the present invention enables industrial production of lactic acid through fixation of carbon dioxide. Lactic acid serves as a raw material for the production of polylactic acid, which is a typical biodegradable plastic, and hence the present invention paves the way for allowing efficient industrial production of polylactic acid through utilization of carbon dioxide.

BRIEF DESCRIPTION OF DRAWINGS

FIG. 1 is a diagram illustrating a method of generating an example of a lactic acid-utilizing enzyme gene-disrupted strain.

DESCRIPTION OF EMBODIMENTS

The present invention is described in detail below.

The recombinant *Hydrogenophilus* bacterium of the present invention is a recombinant *Hydrogenophilus* bacterium which has a lactate dehydrogenase gene and/or a malate/lactate dehydrogenase gene introduced thereinto, and in which one or more of three lactic acid-utilizing enzyme genes on a genome is/are disrupted.

(1) *Hydrogenophilus* Bacteria

Examples of *Hydrogenophilus* bacteria include *Hydrogenophilus thermoluteolus, Hydrogenophilus halorhabdus, Hydrogenophilus denitrificans, Hydrogenophilus hirschii, Hydrogenophilus islandicus*, strain Mar3 of the genus *Hydrogenophilus* (*Hydrogenophilus* sp. Mar3) and strain Z1038 of the genus *Hydrogenophilus* (*Hydrogenophilus* sp. Z1038). In particular, *Hydrogenophilus thermoluteolus* is preferable because its superior growth rate enables top-level carbon fixation from cardon dioxide among carbon dioxide fixing microorganisms.

*Hydrogenophilus* bacteria have been easily isolated from diverse regions everywhere on the earth. A preferable strain of *Hydrogenophilus thermoluteolus* is strain TH-1 (NBRC 14978). *Hydrogenophilus thermoluteolus* strain TH-1 (NBRC 14978) exhibits top-level growth rate among carbon dioxide fixing microorganisms (Agricultural and Biological Chemistry, 41, 685-690 (1977)). *Hydrogenophilus thermoluteolus* strain NBRC 14978 is internationally deposited under the Budapest Treaty, and is thus available to the general public.

(2) Lactic Acid-Utilizing Enzyme Genes (2-1) Wild-Type Lactic Acid-Utilizing Enzyme Genes A wild-type *Hydrogenophilus* bacterium has three lactic acid-utilizing enzyme genes on the genome, and polypeptides encoded by these genes form a lactic acid-utilizing enzyme complex (conceived to be a lactate oxidase complex). The wild-type *Hydrogenophilus* bacterium produces a lactic acid-utilizing enzyme complex having activity, and thus has a lactic acid-utilizing ability.

The three wild-type lactic acid-utilizing enzyme genes are formed of DNA of any one of the following (a1) to (a6), DNA of any one of the following (b1) to (b6), and DNA of any one of the following (c1) to (c6), respectively.

(a1) DNA formed of a base sequence set forth in SEQ ID NO: 1;

(a2) DNA that is formed of a base sequence having 90% or more identity to the base sequence set forth in SEQ ID NO: 1, and that encodes a polypeptide having lactic acid-utilizing enzyme activity;

(a3) DNA that hybridizes with DNA formed of a base sequence complementary to SEQ ID NO: 1 under stringent conditions, and that encodes a polypeptide having lactic acid-utilizing enzyme activity;

(a4) DNA encoding a polypeptide formed of an amino acid sequence set forth in SEQ ID NO: 2;

(a5) DNA encoding a polypeptide that is formed of an amino acid sequence having 90% or more identity to SEQ ID NO: 2, and that has lactic acid-utilizing enzyme activity; and (a6) DNA encoding a polypeptide that is formed of an amino acid sequence having one or a plurality of amino acids deleted, substituted, or added in the amino acid sequence set forth in SEQ ID NO: 2, and that has lactic acid-utilizing enzyme activity.

SEQ ID NO: 1 sets forth the base sequence of the HPTL_1694 gene of the wild strain of *Hydrogenophilus thermoluteolus*, and SEQ ID NO: 2 sets forth the amino acid sequence of the polypeptide encoded by the HPTL_1694 gene of the wild strain of *Hydrogenophilus thermoluteolus*.

(b1) DNA formed of a base sequence set forth in SEQ ID NO: 3;

(b2) DNA that is formed of a base sequence having 90% or more identity to the base sequence set forth in SEQ ID NO: 3, and that encodes a polypeptide having lactic acid-utilizing enzyme activity;

(b3) DNA that hybridizes with DNA formed of a base sequence complementary to SEQ ID NO: 3 under stringent conditions, and that encodes a polypeptide having lactic acid-utilizing enzyme activity;

(b4) DNA encoding a polypeptide formed of an amino acid sequence set forth in SEQ ID NO: 4;

(b5) DNA encoding a polypeptide that is formed of an amino acid sequence having 90% or more identity to SEQ ID NO: 4, and that has lactic acid-utilizing enzyme activity; and (b6) DNA encoding a polypeptide that is formed of an amino acid sequence having one or a plurality of amino acids deleted, substituted, or added in the amino acid sequence set forth in SEQ ID NO: 4, and that has lactic acid-utilizing enzyme activity.

SEQ ID NO: 3 sets forth the base sequence of the HPTL_1695 gene of the wild strain of *Hydrogenophilus thermoluteolus*, and SEQ ID NO: 4 sets forth the amino acid sequence of the polypeptide encoded by the HPTL_1695 gene of the wild strain of *Hydrogenophilus thermoluteolus*.

(c1) DNA formed of a base sequence set forth in SEQ ID NO: 5;

(c2) DNA that is formed of a base sequence having 90% or more identity to the base sequence set forth in SEQ ID NO: 5, and that encodes a polypeptide having lactic acid-utilizing enzyme activity;

(c3) DNA that hybridizes with DNA formed of a base sequence complementary to SEQ ID NO: 5 under stringent conditions, and that encodes a polypeptide having lactic acid-utilizing enzyme activity;

(c4) DNA encoding a polypeptide formed of an amino acid sequence set forth in SEQ ID NO: 6;

(c5) DNA encoding a polypeptide that is formed of an amino acid sequence having 90% or more identity to SEQ ID NO: 6, and that has lactic acid-utilizing enzyme activity; and (c6) DNA encoding a polypeptide that is formed of an amino acid sequence having one or a plurality of amino acids deleted, substituted, or added in the amino acid sequence set forth in SEQ ID NO: 6, and that has lactic acid-utilizing enzyme activity.

SEQ ID NO: 5 sets forth the base sequence of the HPTL_1696 gene of the wild strain of *Hydrogenophilus thermoluteolus*, and SEQ ID NO: 6 sets forth the amino acid sequence of the polypeptide encoded by the HPTL_1696 gene of the wild strain of *Hydrogenophilus thermoluteolus*.

In the present invention, the identities of each of the base sequences and the amino acid sequences are values calculated with GENETYX ver. 17 (manufactured by Genetyx Corporation).

In the present invention, the term "stringent conditions" refers to the following conditions: hybridization performed in a hybridization solution having a salt concentration of 6×SSC under the temperature from 50° C. to 60° C. for 16 hours, after which washing is performed in a solution having a salt concentration of 0.1×SSC.

The DNA of (a2), (b2), or (c2) is preferably formed of a base sequence having 95% or more, especially 98% or more, especially 99% or more identity to the base sequence set forth in SEQ ID NO: 1, 3, or 5, respectively.

The DNA of (a5), (b5), or (c5) preferably encodes a polypeptide formed of an amino acid sequence having 95% or more, especially 98% or more, especially 99% or more identity to the amino acid sequence set forth in SEQ ID NO: 2, 4, or 6, respectively.

In the present invention, the number of "one or a plurality of amino acids" is, for example, from 1 to 5, especially from 1 to 3, especially 1 or 2, in particular, 1. The plurality encompasses several.

The fact that a polypeptide to be tested has lactic acid-utilizing enzyme activity is verified by subjecting the polypeptide to be tested and the other two wild-type lactic acid-utilizing enzymes to a reaction with 5 mM lactic acid in the presence of 120 µg/mL of phenazine methosulfate (PMS) and 60 µg/mL of 3-(4,5-dimethylthiazolyl-2)-2,5-diphenyltetrazolium bromide (MTT), and detecting an increase in absorbance at 570 nm. Along with a lactate oxidase reaction in which lactic acid is oxidized into pyruvic acid, MTT is reduced into formazan in the presence of PMS, and hence the absorbance at 570 nm is increased. When the polypeptide to be tested shows increased absorbance at 570 nm even slightly, it is judged that the formed lactic acid-utilizing enzyme complex shows lactate oxidase activity, and hence it is judged that the polypeptide to be tested has lactic acid-utilizing enzyme activity.

For example, when the polypeptide to be tested is a polypeptide encoded by a base sequence similar to SEQ ID NO: 1, the polypeptide to be tested, the polypeptide encoded by SEQ ID NO: 2, and the polypeptide encoded by SEQ ID NO: 3 are subjected to a reaction with lactic acid in the presence of PMS and MTT.

(2-2) Disruption of Lactic Acid-Utilizing Enzyme Gene

In the recombinant *Hydrogenophilus* bacterium of the present invention, any one or more of the above-mentioned three lactic acid-utilizing enzyme genes on the genome are disrupted. As a result, a lactic acid-utilizing enzyme complex having activity is not formed, or the activity is lower than that of the wild-type lactic acid-utilizing enzyme complex.

In the present invention, the fact that the recombinant *Hydrogenophilus* bacterium does not form a lactic acid-utilizing enzyme complex having activity or forms a lactic acid-utilizing enzyme complex having lower activity than the wild-type lactic acid-utilizing enzyme complex may be verified by the fact that the recombinant *Hydrogenophilus* bacterium cannot grow in a medium containing lactic acid as a sole carbon source or has a lower growth rate than the wild strain.

In order to disrupt a lactic acid-utilizing enzyme gene, it is typically appropriate to delete the whole or part of the lactic acid-utilizing enzyme gene. The lactic acid-utilizing enzyme gene may be disrupted by inserting some nucleotide, oligonucleotide, or polynucleotide into the gene. When the gene disruption is performed by homologous recombination to be described later, it is appropriate to insert a positive selection marker gene into the lactic acid-utilizing enzyme gene. The whole or part of the lactic acid-utilizing enzyme gene may be substituted with another nucleotide, oligonucleotide, or polynucleotide.

As described above, it is appropriate that the lactic acid-utilizing enzyme gene be disrupted by a deletion, an addition (including an insertion), a substitution, or a combination thereof, of one or a plurality of nucleotides (hereinafter sometimes referred to as "mutation"). When a deletion, an addition (including an insertion), or a substitution of a plurality of nucleotides is introduced, the mutation may be introduced at one site in the gene, or may be dispersedly introduced at a plurality of sites therein.

It is preferred that the number of nucleotides to be deleted, added (including an insertion), or substituted be 3 or more, especially 5 or more, especially 10 or more, especially 20 or more, especially 50 or more. It is preferred that nucleotides in a number corresponding to 1% or more, especially 5% or more, especially 10% or more, especially 50% or more of the full length of the gene be deleted, added (including an insertion), or substituted. This ensures the disruption of the lactic acid-utilizing enzyme gene. The full length of the lactic acid-utilizing enzyme gene (i.e., 100% of the number of constituent nucleotides of the lactic acid-utilizing enzyme gene) may be deleted or substituted. In the case of the addition (including an insertion), for example, up to 100,000 nucleotides may be added. Up to 1,000 or up to 100 nucleotides may be added.

Except when the whole of the lactic acid-utilizing enzyme gene is deleted, the above-mentioned mutation is desirably introduced at a site other than a region encoding the vicinity of the C-terminus of the lactic acid-utilizing enzyme. This facilitates the loss or lowering of the function of the lactic acid-utilizing enzyme gene. For example, the above-mentioned mutation is desirably introduced into a region encoding 95% or less, especially 90% or less, especially 80% or less with respect to the full length from the N-terminus of the lactic acid-utilizing enzyme. When a region encoding the vicinity of the N-terminus of the lactic acid-utilizing enzyme is mutated, in many cases, the polypeptide is not expressed or the polypeptide does not have a normal higher order structure, and hence the above-mentioned mutation may be introduced into the region encoding the vicinity of the N-terminus of the lactic acid-utilizing enzyme.

For example, a lactic acid-utilizing enzyme gene on a chromosome may be substituted with a disrupted lactic acid-utilizing enzyme gene by generating the disrupted gene through PCR or the like, and introducing the disrupted gene into a parental strain to cause homologous recombination between the disrupted gene and the gene on the genome.

A homologous recombination-based gene disruption method itself is well known, but the modification of a gene on a genome through utilization of homologous recombination is unprecedented in a *Hydrogenophilus* bacterium. The inventors of the present invention have identified a hygromycin resistance gene that functions in a *Hydrogenophilus* bacterium and can be used as a positive selection marker, and have identified a streptomycin sensitivity gene that functions in a *Hydrogenophilus* bacterium (in particular, in a streptomycin-resistant strain) and can be used as a counterselection marker. Accordingly, through use of those genes, a lactic acid-utilizing enzyme gene of the *Hydrogenophilus* bacterium can be disrupted by homologous recombination.

In this method, for example, a streptomycin sensitivity gene formed of a base sequence set forth in SEQ ID NO: 7 may be used as the counterselection marker. In this method, for example, a hygromycin resistance gene formed of a base sequence set forth in SEQ ID NO: 8 may be used as the positive selection marker gene that functions in a *Hydrogenophilus* bacterium.

A method of disrupting a lactic acid-utilizing enzyme gene is described below by taking, as an example, a method involving deleting a partial region inside a lactic acid-utilizing enzyme gene. FIG. 1 is an illustration of this method.

It is appropriate that the 5' upstream DNA region of a region to be deleted of a DNA fragment formed of a lactic acid-utilizing enzyme gene of a *Hydrogenophilus* bacterium, and the 3' DNA downstream region of the same region to be deleted be each amplified by performing PCR through use of the genomic DNA of the *Hydrogenophilus* bacterium as a template, and DNA obtained by linking the 5' upstream region and the 3' downstream region to each other be linked to a vector that can be used in a host, such as *Escherichia coli*. The DNA obtained by linking the 5' upstream region and 3' downstream region of the region to be deleted to each other is DNA in which the inside of the lactic acid-utilizing enzyme gene has been deleted.

In order to improve homologous recombination efficiency, it is preferred that the 5' upstream DNA region and the 3' downstream DNA region be composed of 10 or more nucleotides, preferably 50 or more nucleotides, more preferably 100 or more nucleotides. Alternatively, the DNAs to be linked to each other do not need to be formed of base sequences completely identical to the 5' upstream region of the region to be deleted and the 3' downstream region of the region to be deleted, respectively, and as the lengths of the regions to be used for homologous recombination increase, homologous recombination can be caused with lower identity to the 5' upstream region or 3' downstream region of the region to be deleted.

Then, a marker cassette to be inserted between the 5' upstream region and 3' downstream region of the region to be deleted, which are linked to each other on the vector, is produced. Herein, the marker cassette is such that a streptomycin sensitivity gene that functions in the *Hydrogenophilus* bacterium and a hygromycin resistance gene that functions in the *Hydrogenophilus* bacterium are linked to each other adjacently or with DNA of about 10,000 base pairs or less being interposed therebetween.

Then, it is appropriate that the marker cassette be inserted between the 5' upstream region and 3' downstream region of the region to be deleted, which are on the vector having inserted thereinto the DNA fragment in which the inside of the lactic acid-utilizing enzyme gene has been deleted. Further, it is appropriate that, in accordance with a conventional method, the host be transformed with the resultant vector, and the vector be extracted from the transformant.

Then, it is appropriate that the vector be linearized through cleavage of part of the vector or a boundary between the vector and the 5' upstream region or the 3' downstream region with a restriction enzyme, to thereby provide a labeling DNA fragment. The cleavage is performed so that the marker cassette is brought into a state of being interposed between the 5' upstream region and 3' downstream region of the region to be deleted. Thus, a labeling DNA fragment having inserted thereinto the marker cassette in which a DNA fragment containing the streptomycin sensitivity gene and a DNA fragment containing the hygromycin resistance gene are linked to each other is obtained.

It is appropriate that an operation of introducing the labeling DNA fragment into the streptomycin-resistant strains of the *Hydrogenophilus* bacterium be performed, and recombinants in each of which the lactic acid-utilizing enzyme gene of the streptomycin-resistant strain has been substituted with the labeling DNA fragment be selected through use of the presence of hygromycin resistance as an indicator.

The introduction of DNA into cells of the *Hydrogenophilus* bacterium may be performed by a known method, such as a calcium chloride method, a calcium phosphate method, a DEAE-dextran mediated transfection method, or an electric pulse method.

Then, in order to eliminate the marker cassette inserted into the lactic acid-utilizing enzyme gene, an inside segment of which has been deleted, homologous recombination is performed using the previously generated DNA fragment in which a segment within the lactic acid-utilizing enzyme gene has been deleted.

The vector having inserted thereinto the lactic acid-utilizing enzyme gene an inside segment of which has been deleted is linearized by being cleaved in such a manner as not to divide the deleted lactic acid-utilizing enzyme gene. It is appropriate that an operation of introducing the linear DNA fragment into the streptomycin-sensitive strains (recombinants in each of which the lactic acid-utilizing enzyme gene has been substituted with the labeling DNA fragment) be performed, and a strain that has become streptomycin-resistant be selected. It is also preferred that a strain that is streptomycin-resistant and has lost the hygromycin resistance be selected. Thus, a recombinant from which the marker cassette inserted into the lactic acid-utilizing enzyme gene has been eliminated, that is, a recombinant with a deletion within the lactic acid-utilizing enzyme gene is obtained.

It is appropriate that the base sequence of the lactic acid-utilizing enzyme gene of the resultant recombinant be determined to verify the deletion of the inside of the gene.

With the segment within the lactic acid-utilizing enzyme gene is deleted, the recombinant has a reduced growth rate in a medium using lactic acid as a sole carbon source as compared to the parental strain of the *Hydrogenophilus* bacterium, or does not grow therein.

(3) Transformant of Lactic Acid-Utilizing Enzyme Gene-Disrupted Strain (3-1) Lactate Dehydrogenase Gene • Malate/Lactate Dehydrogenase Gene The recombinant of the present invention is a recombinant that is the lactic acid-utilizing enzyme gene-disrupted strain of the *Hydrogenophilus* bacterium described above, and that has a lactate dehydrogenase gene and/or a malate/lactate dehydrogenase gene introduced thereinto. In other words, this recombinant has a lactic acid-utilizing enzyme gene on the genome disrupted, and has an exogenous lactate dehydrogenase gene and/or malate/lactate dehydrogenase gene. The malate/lactate dehydrogenase is an enzyme having lactate dehydrogenase activity. Two or more kinds of the lactate dehydrogenase genes may be introduced, and two or more kinds of the malate/lactate dehydrogenase genes may be introduced.

The lactic acid-utilizing enzyme gene on the genome of the wild-type *Hydrogenophilus* bacterium may be disrupted before the lactate dehydrogenase gene and/or the malate/lactate dehydrogenase gene is introduced, or the lactate dehydrogenase gene and/or the malate/lactate dehydrogenase gene may be introduced into the wild-type *Hydrogenophilus* bacterium before the lactic acid-utilizing enzyme gene on the genome is disrupted.

The lactate dehydrogenase gene is preferably (d1) the ldh gene of *Parageobacillus thermoglucosidasius*, the ldh gene of *Geobacillus kaustophilus*, or the ldh gene of *Thermus thermophilus* from the viewpoint of good lactic acid production efficiency.

The base sequence of the ldh gene of *Parageobacillus thermoglucosidasius* is set forth in SEQ ID NO: 9, the base sequence of the ldh gene of *Geobacillus kaustophilus* is set forth in SEQ ID NO: 10, and the base sequence of the ldh gene of *Thermus thermophilus* is set forth in SEQ ID NO: 11.

(d2) DNA that is formed of a base sequence having 90% or more, especially 95% or more, especially 98% or more, especially 99% or more identity to DNA formed of the base sequence set forth in SEQ ID NO: 9, 10, or 11, and that encodes a polypeptide having lactate dehydrogenase activity may also be preferably used.

(d3) DNA that hybridizes with DNA formed of a base sequence complementary to SEQ ID NO: 9, 10, or 11 under stringent conditions, and that encodes a polypeptide having lactate dehydrogenase activity may also be preferably used.

(d4) DNA encoding a polypeptide formed of an amino acid sequence set forth in SEQ ID NO: 12, 13, or 14 may also be preferably used. SEQ ID NO: 12 sets forth the amino acid sequence of the lactate dehydrogenase of *Parageobacillus thermoglucosidasius*, SEQ ID NO: 13 sets forth the amino acid sequence of the lactate dehydrogenase of *Geobacillus kaustophilus*, and SEQ ID NO: 14 sets forth the amino acid sequence of the lactate dehydrogenase of *Thermus thermophilus*.

(d5) DNA encoding a polypeptide that is formed of an amino acid sequence having 90% or more, especially 95% or more, especially 98% or more, especially 99% or more identity to SEQ ID NO: 12, 13, or 14, and that has lactate dehydrogenase activity may also be preferably used.

(d6) DNA encoding a polypeptide that is formed of an amino acid sequence having one or a plurality of amino acids deleted, substituted, or added in the amino acid sequence set forth in SEQ ID NO: 12, 13, or 14, and that has lactate dehydrogenase activity may also be preferably used.

The malate/lactate dehydrogenase gene is preferably (e1) any one of the mldh gene of *Thermus thermophilus*, and the mldh-1 and mldh-2 genes of *Meiothermus ruber* from the viewpoint of good lactic acid production efficiency.

The base sequence of the mldh gene of *Thermus thermophilus* is set forth in SEQ ID NO: 15, the base sequence of the mldh-1 gene of *Meiothermus ruber* is set forth in SEQ ID NO: 16, and the base sequence of the mldh-2 gene of *Meiothermus ruber* is set forth in SEQ ID NO: 17.

(e2) DNA that is formed of a base sequence having 90% or more, especially 95% or more, especially 98% or more, especially 99% or more identity to DNA formed of the base sequence set forth in SEQ ID NO: 15, 16, or 17, and that encodes a polypeptide having lactate dehydrogenase activity, or (e3) DNA that hybridizes with DNA formed of a base sequence complementary to SEQ ID NO: 15, 16, or 17 under stringent conditions, and that encodes a polypeptide having lactate dehydrogenase activity may also be preferably used.

The malate/lactate dehydrogenase has both malate dehydrogenase activity and lactate dehydrogenase activity, but in the present invention, the malate/lactate dehydrogenase is identified by the presence of lactate dehydrogenase activity.

(e4) DNA encoding a polypeptide formed of an amino acid sequence set forth in SEQ ID NO: 18, 19, or 20 may also be preferably used. SEQ ID NO: 18 sets forth the amino acid sequence encoded by the malate/lactate dehydrogenase (Mldh) gene of *Thermus thermophilus*, SEQ ID NO: 19 sets forth the amino acid sequence encoded by the malate/lactate dehydrogenase (Mldh-1) gene of *Meiothermus ruber*, and SEQ ID NO: 20 sets forth the amino acid sequence encoded by the malate/lactate dehydrogenase (Mldh-2) gene of *Meiothermus ruber*.

(e5) DNA encoding a polypeptide that is formed of an amino acid sequence having 90% or more, especially 95% or more, especially 98% or more, especially 99% or more identity to SEQ ID NO: 18, 19, or 20, and that has lactate dehydrogenase activity, or (e6) DNA encoding a polypeptide that is formed of an amino acid sequence having one or a plurality of amino acids deleted, substituted, or added in the amino acid sequence set forth in SEQ ID NO: 18, 19, or 20, and that has lactate dehydrogenase activity may also be preferably used.

In the present invention, the fact that a polypeptide has lactate dehydrogenase activity is verified by subjecting the polypeptide to be tested to a reaction with pyruvic acid in the presence of NADH, and detecting a reduction in absorbance at 340 nm. The lactate dehydrogenase produces lactic acid from pyruvic acid. The lactate dehydrogenase consumes NADH in the production of lactic acid from pyruvic acid, and hence a reduction in NADH amount is detected using a reduction in absorbance at 340 nm as an indicator. Specifically, a method described in the "Examples" section is performed. When the polypeptide to be tested reduces the absorbance at 340 nm even slightly, it is judged that the polypeptide has lactate dehydrogenase activity.

(3-2) Lactate Permease Gene

The present invention encompasses a recombinant that is the lactic acid-utilizing enzyme gene-disrupted strain of the *Hydrogenophilus* bacterium described above, and that has a lactate dehydrogenase gene and/or a malate/lactate dehydrogenase gene, and a lactate permease gene introduced thereinto. In other words, the recombinant has a lactic acid-utilizing enzyme gene on the genome disrupted, and has an exogenous or non-native lactate dehydrogenase gene and/or malate/lactate dehydrogenase gene, and an exogenous or non-native lactate permease gene.

One kind or two or more kinds each of the lactate dehydrogenase genes, the malate/lactate dehydrogenase genes, and the lactate permease genes may be introduced.

The lactic acid-utilizing enzyme gene on the genome of the wild-type *Hydrogenophilus* bacterium may be disrupted before the lactate dehydrogenase gene and/or the malate/lactate dehydrogenase gene, and the lactate permease gene are introduced, or the lactate dehydrogenase gene and/or the malate/lactate dehydrogenase gene, and the lactate permease gene may be introduced into the wild-type *Hydrogenophilus* bacterium before the lactic acid-utilizing enzyme gene on the genome is disrupted. The lactate dehydrogenase gene and/or the malate/lactate dehydrogenase gene may be introduced into the wild-type *Hydrogenophilus* bacterium before the lactic acid-utilizing enzyme gene on the genome is disrupted, followed by the introduction of the lactate permease gene, or the lactate permease gene may be introduced into the wild-type *Hydrogenophilus* bacterium before the lactic acid-utilizing enzyme gene on the genome is disrupted, followed by the introduction of the lactate dehydrogenase gene and/or the malate/lactate dehydrogenase gene.

The lactate permease gene is preferably (f1) the lutP gene of *Geobacillus kaustophilus* from the viewpoint of good efficiency of the secretion of lactic acid by the lactic acid-utilizing enzyme gene-disrupted strain of the *Hydrogenophilus* bacterium.

The base sequence of the lutP gene of *Geobacillus kaustophilus* is set forth in SEQ ID NO: 21.

(f2) DNA that is formed of a base sequence having 90% or more, especially 95% or more, especially 98% or more, especially 99% or more identity to DNA formed of the base sequence set forth in SEQ ID NO: 21, and that encodes a polypeptide having lactate permease activity may also be preferably used.

(f3) DNA that hybridizes with DNA formed of a base sequence complementary to SEQ ID NO: 21 under stringent conditions, and that encodes a polypeptide having lactate permease activity may also be preferably used.

(f4) DNA encoding a polypeptide formed of an amino acid sequence set forth in SEQ ID NO: 22 may also be preferably used. SEQ ID NO: 22 sets forth the amino acid sequence of the lactate permease (LutP) of *Geobacillus kaustophilus*.

(f5) DNA encoding a polypeptide that is formed of an amino acid sequence having 90% or more, especially 95% or more, especially 98% or more, especially 99% or more identity to SEQ ID NO: 22, and that has lactate permease activity may also be preferably used.

(f6) DNA encoding a polypeptide that is formed of an amino acid sequence having one or a plurality of amino acids deleted, substituted, or added in the amino acid sequence set forth in SEQ ID NO: 22, and that has lactate permease activity may also be preferably used.

In the present invention, the fact that a polypeptide to be tested has lactate permease activity is verified by the fact that, when DNA encoding the polypeptide to be tested is introduced into *Escherichia coli*, followed by culture, the production amount of lactic acid in the culture supernatant is increased as compared to that of the host before the introduction. *Escherichia coli* is used as the host because *Escherichia coli* has a lactate dehydrogenase gene and produces lactic acid.

(3-3) Method of Producing Transformant

Description is given of a method of obtaining a transformant, including introducing a lactate dehydrogenase gene and/or a malate/lactate dehydrogenase gene, and a lactate permease gene into a wild strain or a lactic acid-utilizing enzyme gene-disrupted strain of a *Hydrogenophilus* bacterium serving as a host.

Plasmid vectors for introducing the above-described DNAs into a host should contain a DNA which controls the autonomous replication function within *Hydrogenophilus* bacteria, and examples include broad-host-range vector pRK415 (GenBank: EF437940.1), pBHR1 (GenBank: Y14439.1), pMMB67EH (ATCC 37622), pCAR1 (NCBI Reference Sequence: NC_004444.1), pC194 (NCBI Reference Sequence: NC_002013.1), pK18mobsacB (GenBank: FJ437239.1), pUB110 (NCBI Reference Sequence: NC_001384.1), and the like.

Examples of preferable promoters include tac promoter, lac promoter, trc promoter, or each of promoters OXB1 and OXB11 to OXB20 from Oxford Genetics Ltd. Examples of preferable terminators include the T1T2 terminator of *Escherichia coli* rRNA operon rrnB, the t0 transcription terminator of bacteriophage λ, T7 terminator, and the like.

Transformation can be carried out by publicly known methods such as calcium chloride method, calcium phosphate method, DEAE-dextran transfection method, and electric pulse method.

*Hydrogenophilus* bacteria grow under autotrophic conditions. However, since they can grow under heterotrophic conditions as well, the culture medium which is used to culture a *Hydrogenophilus* bacterium, a lactic acid-utilizing enzyme gene-disrupted strain of the *Hydrogenophilus* bacterium or a *Hydrogenophilus* bacterium transformant can either be an inorganic culture medium or an organic culture medium. An organic culture medium comprising sugar, organic acids, amino acid, and the like can be used. However, the lactic acid-utilizing enzyme gene-disrupted strain does not have lactic acid-utilizing capacity or has a reduced lactic acid-utilizing capacity, therefore, it is desired that a medium containing lactic acid as a sole carbon source is not used for culturing the strain. The pH of the culture medium can be adjusted to approximately 6.2 to 8.

In any of the cases, culture can be carried out while supplying a mixture of gases containing hydrogen, oxygen, and carbon dioxide, and preferably a mixture of gases consisting of hydrogen, oxygen, and carbon dioxide. When using an organic culture medium, a mixture of gases containing hydrogen, oxygen, and carbon dioxide, for example air, can be used for aeration. When carbon dioxide gas is not supplied, a culture medium containing a carbonate as a carbon source can be used. Mixed gases can be entrapped within or continuously supplied into an airtight culture container, and can be dissolved into the culture medium by means of shaking culture. Alternatively, the culture container can be an airtight or open type, and mixed gases can be dissolved into the culture medium by bubbling.

The volume ratio of hydrogen, oxygen, and carbon dioxide within the supplied gas (hydrogen: oxygen: carbon dioxide) is preferably 1.75 to 7.5:1:0.25 to 3, more preferably 5 to 7.5:1:1 to 2, and furthermore preferably 6.25 to 7.5:1:1.5. *Hydrogenophilus* bacteria are thermophilic bacteria, and thus the culture temperature is preferably 35 to 55° C., more preferably 37 to 52° C., and even more preferably 50 to 52° C.

When the lactate dehydrogenase gene and/or the malate/lactate dehydrogenase gene, and the lactate permease gene are both introduced into the lactic acid-utilizing enzyme gene-disrupted strain, the lactate permease gene may be introduced by cloning the lactate dehydrogenase gene and/or the malate/lactate dehydrogenase gene, and the lactate permease gene into the same plasmid vector, or may be introduced by being cloned into a different plasmid vector.

The lactate dehydrogenase gene, the malate/lactate dehydrogenase gene, and the lactate permease gene may each be incorporated onto the genome of the lactic acid-utilizing enzyme gene-disrupted strain of the *Hydrogenophilus* bacterium by homologous recombination or the like.

(4) Method for Producing Lactic Acid

When producing lactic using the transformant of a *Hydrogenophilus* bacterium described above, the transformant can be cultured using an inorganic or organic culture medium while supplying a mixture of gases containing hydrogen, oxygen, and carbon dioxide.

The supplied gas is preferably a mixture of gases consisting of hydrogen, oxygen, and carbon dioxide. However, different kinds of gases can be mixed within, to the extent that lactic acid can be produced efficiently.

*Hydrogenophilus* bacteria can grow using hydrogen as a source of energy and using carbon dioxide as a sole carbon source, and thus, carbon dioxide can be fixed efficiently particularly by producing the above-described compounds by using substantially only carbon dioxide (in particular, by using only carbon dioxide) as a carbon source. Therefore, using an inorganic culture medium that does not contain carbon sources such as organic substances and carbonates, namely, carrying out culture using substantially only carbon dioxide (in particular, using only carbon dioxide) as a carbon source is preferable. "Using substantially only carbon dioxide as a carbon source" encompasses cases in which an unavoidable amount of other carbon sources is mixed within. Furthermore, a culture medium containing organic substances such as sugar, organic acids, and amino acids, as well as carbonates, can also be used without supplying carbon dioxide.

The pH of the culture medium is preferably 6.2 to 8, more preferably 6.4 to 7.4, and furthermore preferably 6.6 to 7. When the pH is within this range, bacteria grow well and mixed gas dissolves well into the culture medium, and lactic acid can be produced efficiently.

When batch culture is utilized, mixed gases can be entrapped within an airtight culture container and static culture or shaking culture can be carried out. When continuous culture is utilized, mixed gases can be continuously supplied into an airtight culture container and shaking culture can be carried out, or the recombinant can be cultured using an airtight culture container while introducing mixed gases into the culture medium by bubbling. Shaking culture is preferable in that better dissolution of mixed gases into the culture medium can be achieved.

The volume ratio of hydrogen, oxygen, and carbon dioxide (hydrogen: oxygen: carbon dioxide) in the supplied gas mixture is preferably 1.75 to 7.5:1:0.25 to 3, more preferably 5 to 7.5:1:1 to 2, and even more preferably 6.25 to 7.5:1:1.5. When the volume ratio is within this range, bacteria grow well, and the target compound can be produced efficiently.

The supply rate of mixed gases or raw material gases can be 10.5 to 60 L/hour, in particular 10.5 to 40 L/hour, in particular 10.5 to 21 L/hour, per 1 L of culture medium. When the supply rate is within this range, transformants grow well and the target compound can be produced efficiently, and the amount of wasted mixed gases can be reduced.

The culture temperature is preferably 35 to 55° C., more preferably 37 to 52° C., and even more preferably 50 to 52° C. When the temperature is within this range, transformants grow well, and lactic acid can be produced efficiently.

The target compound lactic acid is produced in the reaction solution by culturing in the above-described manner. Collecting the reaction solution will enable the recovery of lactic acid, however, lactic acid can furthermore be separated from the reaction solution by following publicly known methods. Such publicly known methods include precipitation method, fractional distillation and electrodialysis.

Examples

The present invention will next be described in further detail with reference to examples, but the present invention is not limited to them.

(1) Acquisition of Streptomycin-Resistant Strain

A *Hydrogenophilus thermoluteolus* TH-1 strain (NBRC 14978) (hereinafter sometimes referred to as "TH-1 strain") was inoculated into a test tube having placed therein 5 mL of A-liquid medium [having 3.0 g of $(NH_4)_2SO_4$, 1.0 g of $KH_2PO_4$, 2.0 g of $K_2HPO_4$, 0.25 g of NaCl, 0.014 g of $FeSO_4.7H_2O$, 0.5 g of $MgSO_4.7H_2O$, 0.03 g of $CaCl_2$, 4.0 mg of $MoO_3$, 28 mg of $ZnSO_4.7H_2O$, 2.0 mg of $CuSO_4.5H_2O$, 4.0 mg of $H_3BO_3$, 4.0 mg of $MnSO_4.5H_2O$, and 4.0 mg of $CoCl_2.6H_2O$ dissolved in 1 L of distilled water (pH 7.0)] using a platinum loop, the test tube was filled with a mixed gas of $H_2:O_2:CO_2=7.5:1:1.5$, and shaking culture was performed at 50° C. The culture liquid after 24 hours was applied to A-solid medium containing 500 μg/mL of streptomycin [having 3.0 g of $(NH_4)_2SO_4$, 1.0 g of $KH_2PO_4$, 2.0 g of $K_2HPO_4$, 0.25 g of NaCl, 0.014 g of $FeSO_4.7H_2O$, 0.5 g of $MgSO_4.7H_2O$, 0.03 g of $CaCl_2$, 4.0 mg of $MoO_3$, 28 mg of $ZnSO_4.7H_2O$, 2.0 mg of $CuSO_4.5H_2O$, 4.0 mg of $H_3BO_3$, 4.0 mg of $MnSO_4.5H_2O$, 4.0 mg of $CoCl_2.6H_2O$, and 15 g of agar dissolved in 1 L of distilled water (pH 7.0)], and culture was performed in a chamber filled with a mixed gas of $H_2:O_2:CO_2=7.5:1:1.5$ at 50° C. for 60 hours.

As a result, the formation of three colonies was able to be recognized on the A-solid medium containing 500 μg/mL of streptomycin. Those grown strains were streptomycin-resistant strains of the TH-1 strain, and one of the strains was named NOC269 strain.

(2) Construction of Marker Cassette

(2-1) Preparation of Counterselection Marker

Genomic DNA was extracted from the wild strain (streptomycin-sensitive strain) of the TH-1 strain in accordance with a conventional method. Through use of the extracted genomic DNA as a template, a DNA fragment containing a rpsL gene, which was a streptomycin sensitivity gene, encoding ribosomal protein S12, was amplified by a PCR method. The following primers were used for the PCR. The PCR was performed by a conventional method using "DNA Thermal Cycler" manufactured by Life Technologies Corporation and using KOD FX Neo (manufactured by Toyobo Co., Ltd.) as a reaction reagent.

Primers for Amplifying Wild-Type rpsL Gene of TH-1 Strain (a-1)
(SEQ ID NO: 23)
5'-ATACGCGTCCTCCGATGCGTCGTAAGGGAAACGTC-3'

(b-1)
(SEQ ID NO: 24)
5'-ATAGTCGACTTATTTCTTGCCCGCAGCGGCGCCCG-3'

The primer (a-1) has an MluI restriction enzyme site added thereto, and the primer (b-1) has a SalI restriction enzyme site added thereto.

(2-2) Preparation of Positive Selection Marker

Through use of DNA of a plasmid pJR225 (GenBank: K01193) [Gene, 25, 179-188 (1983)] containing a hygromycin resistance gene (hereinafter sometimes referred to as "hph") sequence as a template, a DNA fragment containing the hph gene was amplified by a PCR method. The following primers were used for the PCR. The PCR was performed by a conventional method using "DNA Thermal Cycler" manufactured by Life Technologies Corporation and using KOD FX Neo (manufactured by Toyobo Co., Ltd.) as a reaction reagent.

Primers for Amplifying hph Gene (a-2)
(SEQ ID NO: 25)
5'-ATACTCGAGGAGATGACGTTGGAGGGGCAAGGTCG-3'

(b-2)
(SEQ ID NO: 26)
5'-ATACGCGTCTATTCCTTTGCCCTCGGACGAGTGCT-3'

The primer (a-2) has an XhoI restriction enzyme site added thereto, and the primer (b-2) has an MluI restriction enzyme site added thereto.

The reaction liquid produced by each PCR described above was subjected to electrophoresis using 1% agarose gel. As a result, when the genomic DNA of the TH-1 strain was used as a template, an about 0.5-kbp DNA fragment corresponding to the rpsL gene was detected, and when the pJR225 plasmid DNA was used as a template, an about 1.0-kbp DNA fragment corresponding to the hph gene was detected.

The thus prepared DNA fragment containing the rpsL gene and DNA fragment containing the hph gene were cleaved with a restriction enzyme SalI and a restriction enzyme XhoI, respectively, and were mixed with an *Escherichia coli* plasmid vector pUC19 (GenBank: M77789.2) that had been cleaved with a restriction enzyme SmaI, followed by ligation to each other using T4 DNA Ligase (manufactured by Takara Bio Inc.).

*Escherichia coli* JM109 was transformed with the resultant ligation solution by a calcium chloride method, and the transformant was applied to LB agar medium containing 50 μg/mL of ampicillin and 50 μg/mL of hygromycin. The grown strain on the medium was subjected to liquid culture by a conventional method, the plasmid DNA was extracted from the culture liquid, and the plasmid was cleaved with a restriction enzyme MluI. Thus, the inserted fragments were identified. As a result, in addition to the about 2.7-kbp DNA fragment of the pUC19 vector, an about 1.5-kbp DNA fragment corresponding to the sequence of the rpsL gene and the hph gene linked to each other was found.

The constructed plasmid containing a marker cassette in which the rpsL gene and the hph gene were linked to each other was named pUC-Sm$^s$•Hm$^r$.

(3) Disruption of Lactic Acid-Utilizing Enzyme Gene of Host

(3-1) Construction of DNA for Disrupting HPTL_1695 Gene

Through use of the genomic DNA of the wild strain of the TH-1 strain as a template, DNA fragments corresponding to 5'-upstream and 3'-downstream regions of a region to be deleted of HPTL_1695 gene were amplified by a PCR method. The following primers were used for the PCR. The PCR was performed by a conventional method using "DNA Thermal Cycler" manufactured by Life Technologies Corporation and using KOD FX Neo (manufactured by Toyobo Co., Ltd.) as a reaction reagent.

Primers for Amplifying the 5'-Upstream Region of a Region to be Deleted of HPTL_1695 Gene (a-3)
(SEQ ID NO: 27)
5'-CGCGAATTCATGGCTACCCAACCCCGCGTCGGTCT-3'

(b-3)
(SEQ ID NO: 28)
5'-CGCACGCGTTGGAGTGCGGCTGGTCATCGGGTGAC-3'

The primer (a-3) has an EcoRI restriction enzyme site added thereto, and the primer (b-3) has an MluI restriction enzyme site added thereto.

Primers for Amplifying the 3'-Downstream Region of a Region to be Deleted of HPTL_1695 Gene

```
(a-4)
                                         (SEQ ID NO: 29)
5'-GCACGCGTCTGCAGAACGGAGGCGAGCGATGAACG-3'

(b-4)
                                         (SEQ ID NO: 30)
5'-CGCGCATGCTCAGGGGATCAAGAAGACGTGCACCC-3'
```

The primer (a-4) has an MluI restriction enzyme site added thereto, and the primer (b-4) has an SphI restriction enzyme site added thereto.

Each of the PCR reaction mixtures described above was subjected to electrophoresis using 1% agarose gel. As a result, approximately 0.8-kbp DNA fragments corresponding to the upstream region and downstream region of the HPTL_1695 gene were respectively detected.

The thus prepared DNA fragment of the upstream region of the HPTL_1695 gene was cleaved with restriction enzymes EcoRI and MluI, and the thus prepared DNA fragment of the downstream region of the HPTL_1695 gene was cleaved with restriction enzymes MluI and SphI. The cleaved products were mixed with a pUC19 vector that had been cleaved with restriction enzymes EcoRI and SphI, followed by ligation to each other using T4 DNA Ligase (manufactured by Takara Bio Inc.).

*Escherichia coli* JM109 was transformed with the resultant ligation solution by the calcium chloride method, and the transformant was applied to LB agar medium containing 50 μg/mL of ampicillin. The grown strain on the medium was subjected to liquid culture by a conventional method, the plasmid DNA was extracted from the culture liquid, and the plasmid was cleaved with restriction enzymes EcoRI and SphI. Thereafter, it was determined whether or not the upstream and downstream regions had been successfully cloned. As a result, 2.7-kbp and 1.6-kbp DNA fragments expected in the case of successful cloning were identified.

In this plasmid, the 5'-upstream region and 3'-downstream region of the HPTL_1695 gene are linked to each other, and a DNA fragment in a state in which a segment within the HPTL_1695 gene has been deleted is cloned. The constructed plasmid containing the DNA fragment in a state in which the HPTL_1695 gene had been deleted was named pΔHPTL_1695.

(3-2) Construction of DNA for Labeling HPTL_1695 Gene

The pUC-Sm$^s$•Hm$^r$ prepared in (2) above was cleaved with the restriction enzyme MluI, and subjected to electrophoresis using 1% agarose gel. After that, an approximately 1.5-kbp DNA fragment of the marker cassette in which the rpsL gene and the hph gene were linked to each other was excised from the agarose gel, and the gel was frozen and thawed. Thereafter, the DNA was recovered from the gel.

The recovered DNA fragment of the marker cassette was mixed with pΔHPTL_1695 generated in (3-1), which had been cleaved with the restriction enzyme MluI, followed by ligation to each other using T4 DNA Ligase (manufactured by Takara Bio Inc.).

*Escherichia coli* JM109 was transformed with the resultant ligation solution by the calcium chloride method, and the transformant was transferred to LB agar medium containing 50 μg/mL of ampicillin and 50 μg/mL of hygromycin. The strain grown on the medium was subjected to liquid culture by a conventional method, the plasmid DNA was extracted from culture liquid, and the plasmid was cleaved with the restriction enzyme MluI. Thus, the inserted fragments were identified. As a result, in addition to the approximately 4.3-kbp DNA fragment of the pΔHPTL_1695 plasmid, an approximately 1.5-kbp DNA fragment corresponding to the sequence of the marker cassette was identified.

The constructed plasmid for labeling the HPTL_1695 gene was named ΔHPTL_1695-Sm$^s$•Hm$^r$.

(3-3) Labeling of HPTL_1695 Gene of Streptomycin-Resistant Strain (Positive Selection)

The circular plasmid pΔHPTL_1695-Sm$^s$•Hm$^r$ prepared in (3-2) was linearized by being cleaved with restriction enzymes EcoRI and SphI. With the resultant linear pΔHPTL_1695-Sm$^s$•Hm$^r$, the NOC269 strain, which was the streptomycin-resistant strain of the TH-1 strain, was transformed by an electric pulse method (electroporation method). The transformant was transferred to A-solid medium containing 100 μg/mL of hygromycin, and was cultured in a chamber filled with a mixed gas of $H_2$:$O_2$:$CO_2$=7.5:1:1.5 at 50° C. for 60 hours.

Each of the grown strains on the A-solid medium was re-streaked onto A-solid medium containing 100 μg/mL of hygromycin or 500 μg/mL of streptomycin, and was cultured in a chamber filled with a mixed gas of $H_2$:$O_2$:$CO_2$=7.5:1:1.5 at 50° C. for 60 hours.

Through use of a hygromycin-resistant and streptomycin-sensitive strain obtained as a result of the foregoing as a template, a DNA region containing the HPTL_1695 gene was amplified by a colony PCR method. The following primers were used for the PCR. The combination of the primers (a-5) and (b-5) is the combination of the primers (a-3) and (b-4) used in (3-1), and amplifies an approximately 2.9-kbp DNA region containing the HPTL_1695 gene through PCR using the genomic DNA of the wild-type TH-1 strain as a template. The PCR was performed by a conventional method using "DNA Thermal Cycler" manufactured by Life Technologies Corporation and using TaKaRa Ex Taq (manufactured by Takara Bio Inc.) as a reaction reagent.

Primers for Amplifying the Region Containing HPTL_1695 Gene

```
(a-5)
                                         (SEQ ID NO: 31)
5'-CGCGAATTCATGGCTACCCAACCCCGCGTCGGTCT-3'

(b-5)
                                         (SEQ ID NO: 32)
5'-CGCGCATGCTCAGGGGATCAAGAAGACGTGCACCC-3'
```

The resultant reaction mixture was subjected to electrophoresis using 1% agarose gel. As a result, an approximately 3.1-kbp DNA fragment corresponding to a sequence having the marker cassette inserted into the HPTL_1695 gene was detected. In this strain, the marker cassette was inserted into the HPTL_1695 gene. That is, the strain in which the HPTL_1695 gene was labeled with the marker was obtained.

(3-4) Disruption of HPTL_1695 Gene (Counterselection)

The circular plasmid pΔHPTL_1695 prepared in (3-1) was linearized by cleaving with restriction enzymes EcoRI and SphI. The HPTL_1695 gene-labeled strain obtained in (3-3), was transformed with the resultant linear pΔHPTL_1695 by an electric pulse method (electroporation method). The transformant was transferred to A-solid medium containing 500 μg/mL of streptomycin, and was cultured in a chamber filled with a mixed gas of $H_2:O_2:CO_2=7.5:1:1.5$ at 50° C. for 60 hours.

Each of the grown strains on the A-solid medium was restreaked onto A-solid medium containing 100 μg/mL of hygromycin or 500 μg/mL of streptomycin, and was cultured in a chamber filled with a mixed gas of $H_2:O_2:CO_2=7.5:1:1.5$ at 50° C. for 60 hours.

Through use of the hygromycin-sensitive and streptomycin-resistant strain obtained as a result of the foregoing as a template, a DNA region containing the HPTL_1695 gene was amplified by colony PCR method. The colony PCR was performed by the same method as in (3-3).

The resultant reaction mixture was subjected to electrophoresis using 1% agarose gel. As a result, an approximately 1.6-kbp DNA fragment to be amplified in the case where the HPTL_1695 gene was substituted with the DNA fragment in a state in which a segment within the HPTL_1695 gene had been deleted of (3-1) was detected. That is, the segment within the HPTL_1695 gene has been deleted, and hence the HPTL_1695 gene has been disrupted. The strain in which the HPTL_1695 gene was disrupted was named NOC373 strain.

In the NOC373 strain, a region of base Nos. 19 to 1410 of the base sequence (SEQ ID NO: 3) of the HPTL_1695 gene of the TH-1 strain is substituted with ACGCGTCTGCAG (SEQ ID NO: 33). This corresponds to a substitution of a region of amino acid Nos. 7 to 470 of the amino acid sequence (SEQ ID NO: 4) of the polypeptide encoded by the HPTL_1695 gene of the TH-1 strain with TRLQ (SEQ ID NO: 34).

(3-5) Determination of Lactic Acid-Utilizing Property of NOC373 Strain

In the NOC373 strain, the HPTL_1695 gene is disrupted. Whether or not the NOC373 strain, in which HPTL_1695 gene was disrupted, had lost a lactic acid-utilizing property was determined as described below.

Each of the NOC373 strain and the NOC269 strain serving as the parental strain of the NOC373 strain was streaked onto A-solid medium containing 30 mM sodium lactate as a sole carbon source, and was cultured at 50° C. for 60 hours. As a result, it was recognized that the NOC269 strain serving as the parental strain grew on the A-solid medium containing 30 mM sodium lactate, but the NOC373 strain, in which the HPTL_1695 gene was disrupted, did not grow at all. That is, the NOC373 strain lost its original lactic acid-utilizing ability through the disruption of the HPTL_1695 gene. Accordingly, it was confirmed that the HPTL_1695 gene was authentically a lactic acid-utilizing enzyme gene.

(4) Introduction of Lactate Dehydrogenase Gene Malate/Lactate Dehydrogenase Gene (4-1) Construction of a Plasmid Vector The method for constructing a plasmid vector that was commonly used to introduce genes for conferring lactic acid producing ability is described below.

First, a broad-host-range vector pRK415 (GenBank: EF437940.1) (Gene, 70, 191-197 (1998)) was used as a template and PCR was performed. In order to amplify the DNA fragment of the plasmid region excluding a tetracycline gene region, a primer pair described below was synthesized and used. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of pRK415 Plasmid Sequence (a-6)
(SEQ ID NO: 35)
5'-CGTGGCCAACTAGGCCCAGCCAGATACTCCCGATC-3'

(b-6)
(SEQ ID NO: 36)
5'-TGAGGCCTCATTGGCCGGAGCGCAACCCACTCACT-3'

A SfiI restriction site has been added to primers (a-6) and (b-6).

Plasmid pK18mobsacB (GenBank: FJ437239.1) (Gene, 145, 69-73 (1994)), which contains a neomycin/kanamycin resistance gene (hereinafter, the gene may be referred to as "nptII"), was used as a template and PCR was performed according to a conventional method. In the PCR, a primer pair described below was synthesized and used in order to amplify the DNA fragment containing the nptII gene sequence. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of nptII Gene Sequence (a-7)
(SEQ ID NO: 37)
5'-ctgGGCCTAGTTGGCCacgtagaaagccagtccgc-3'

(b-7)
(SEQ ID NO: 38)
5'-tccGGCCAATGAGGCCtcagaagaactcgtcaaga-3'

A SfiI restriction site has been added to primers (a-7) and (b-7).

The reaction solutions that were produced by each of the above-described PCR were subjected to electrophoresis using a 1% agarose gel, and as a result, a DNA fragment of approximately 8.7-kb was detected when pRK415 plasmid was used as a template, and a DNA fragment of approximately 1.1-kb was detected when nptII gene was used as a template.

Thus prepared DNA fragments were each cleaved by restriction enzyme SfiI, and reacted with a T4 DNA Ligase (manufactured by Takara Bio Inc.) to obtain a ligation solution. The obtained ligation solution was used to transform *Escherichia coli* JM109 by calcium chloride method (Journal of Molecular Biology, 53, 159-162 (1970)), and the transformants were applied onto LB agar media containing 50 μg/mL kanamycin. Viable strains on the culture media were cultured in a liquid culture medium by a conventional method, and plasmid DNA was extracted from the obtained culture solution. This plasmid DNA was cleaved by using restriction enzyme SfiI, and the inserted fragment was confirmed. As a result, a DNA fragment of the nptII gene sequence which was approximately 1.1-kb was observed in addition to DNA fragments of approximately 2.0-kb, 3.0-kb and 3.7-kb, which were derived from the pRK415 plasmid.

The constructed plasmid was named pCYK01.

(4-2) Construction of Cloning Vector Used for Gene Expression (4-2-1) Preparation of DNA Fragment of λ t0 Terminator Sequence A primer pair described below was synthesized and used in PCR in order to prepare a DNA having λt0 terminator sequence. PCR was performed using "DNA thermal cycler" manufactured by Life Technologies Inc., and using KOD FX Neo (manufactured by Toyobo Co., Ltd.) as a reaction reagent. No template DNA was included since extension was carried out using each primer as the other's template.

Primers for the Preparation of λ t0 Terminator Sequence
(a-8) 5'-

(SEQ ID NO: 39)
GCATTAATccttggactcctgttgatagatccagtaatgacctcagaac
tccatctggatttgttcagaacgctcggttgccg-3'

(b-8)
(SEQ ID NO: 40)
5'-caccgtgcagtcgatgGATctggattctcaccaataaaaaacgccc
ggcggcaaccgagcgttctgaacaaatccagatggag-3'

The base sequences of the 3' ends of primers (a-8) and (b-8) are complementary to each other.

The produced reaction solution was subjected to electrophoresis using a 1% agarose gel, and as a result, a DNA fragment of approximately 0.13-kb, which corresponds to the λ t0 terminator sequence, was detected.

(4-2-2) Preparation of a DNA Fragment of tac Promoter Sequence

PCR was performed using plasmid pMAL-c5X (manufactured by New England Biolabs Inc.) containing a tac promoter, as a template. In the PCR, a primer pair described below was synthesized and used in order to amplify tac promoter sequence. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of Tac Promoter Sequence (a-9)
(SEQ ID NO: 41)
5'-TTATTGGTGAGAATCCAGATCCATCGACTGCACGGTGCACCAATGC
TTCT-3'

(b-9)
(SEQ ID NO: 42)
5'-gcaagcttggagtgatcatcgtATGCATATGCGTTTCTCCTCCAGA
TCCctgtttcctgtgtgaaattgt-3'

The produced reaction solution was subjected to electrophoresis using a 1% agarose gel, and as a result, a DNA fragment of approximately 0.3-kb, which corresponds to tac promoter sequence, was detected.

(4-2-3) Introduction of λ t0 Terminator and Tac Promoter Sequences

The DNA fragments that were prepared in the above-described (4-2-1) and (4-2-2) were cut out from the agarose gel, and DNA was recovered from the gel by freezing and melting the gel. The recovered DNA fragments corresponding to λ t0 terminator sequence and the tac promoter sequence were mixed and used as templates, and overlap extension PCR was performed. In the overlap extension PCR, a combination of the above-described primers (a-8) and (b-9) was used in order to prepare a DNA in which the tac promoter is linked downstream of λt0 terminator. The base sequences of the 5' ends of the primers (b-8) and (a-9), which were used in amplifying the template DNA fragments, are complementary with each other. PshBI and HindIII restriction sites have been added to primers (a-8) and (b-9), respectively.

The produced reaction solution was subjected to electrophoresis using a 1% agarose gel, and as a result, a DNA fragment of approximately 0.4-kb, which corresponds to the DNA in which the tac promoter is linked downstream of λ t0 terminator, was detected.

The approximately 0.4-kb DNA fragment that was amplified by PCR, in which the tac promoter is linked downstream of the λ t0 terminator, and the above-mentioned approximately 9.8-kb DNA fragment of cloning vector pCYK01, were cleaved by the restriction enzymes PshBI and HindIII. The cleaved DNA fragments were linked to each other using a T4 DNA Ligase (manufactured by Takara Bio Inc.).

The obtained ligation solution was used to transform Escherichia coli JM109 by calcium chloride method, and the transformants were applied onto LB agar media containing 50 µg/mL kanamycin. Viable strains on the culture media were cultured in a liquid culture medium by a conventional method, and plasmid DNA was extracted from the obtained culture solution. This plasmid DNA was cleaved by using restriction enzymes PshBI and HindIII, and the inserted fragment was confirmed. As a result, a DNA fragment of approximately 0.4-kb, in which tac promoter is linked downstream of λ t0 terminator, was observed in addition to a DNA fragment of approximately 9.6-kb from plasmid pCYK01.

(4-2-4) Introduction of rrnB T1T2 Bidirectional Terminator (Hereinafter, May be Referred to as "rrnB Terminator")

PCR was performed using plasmid pMAL-c5X (manufactured by New England Biolabs Inc.) containing rrnB terminator sequence as a template. In the PCR, a primer pair described below was synthesized and used in order to amplify rrnB terminator sequence. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of rrnB Terminator Sequence (a-10)
(SEQ ID NO: 43)
5'-ctcgaattcactggccgtcgttttacaacgtcgtg-3'

(b-10)
(SEQ ID NO: 44)
5'-CGCAATTGAGTTTGTAGAAACGCAAAAAGGCCATC-3'

EcoRI and MunI restriction sites have been added to primers (a-10) and (b-10), respectively.

The produced reaction solution was subjected to electrophoresis using a 1% agarose gel, and as a result, a DNA fragment of approximately 0.6-kb, which corresponds to rrnB terminator sequence, was detected.

The approximately 0.6-kb DNA fragment containing rrnB terminator sequence, which was amplified by the above-described PCR, was cleaved by restriction enzymes EcoRI and MunI, and the approximately 10.0-kb DNA fragment of the plasmid that was constructed in the above-described (4-2-3) was cleaved using restriction enzyme EcoRI. The cleaved DNA fragments were linked to each other using a T4 DNA Ligase (manufactured by Takara Bio Inc.).

The obtained ligation solution was used to transform Escherichia coli JM109 by calcium chloride method, and the obtained transformants were applied onto LB agar media containing 50 µg/mL kanamycin. Viable strains on the culture media were cultured in a liquid culture medium by a conventional method, and plasmid DNA was extracted from the obtained culture solution. This plasmid was cleaved by using restriction enzymes EcoRI and MunI, and the inserted fragment was confirmed. As a result, a DNA fragment of approximately 0.6-kb which corresponds to rrnB terminator sequence was observed in addition to a DNA fragment of approximately 10.0-kb from the above-described plasmid of (4-2-3).

The constructed cloning vector for gene expression was named pCYK21.

(4-3) Introduction of Lactate Dehydrogenase Gene Malate/Lactate Dehydrogenase Gene (4-3-1) Cloning of Lactate Dehydrogenase Gene Genomic DNAs were extracted from *Parageobacillus thermoglucosidasius* NBRC 107763, *Geobacillus kaustophilus* NBRC 102445, and *Meiothermus ruber* NBRC 106122 according to a conventional method. Genomic DNA of *Thermus thermophilus* HB8 strain (ATCC 27634) was purchased from Takara Bio Inc.

The four genomic DNAs described above were each used as templates to amplify a DNA fragment containing lactate dehydrogenase ldh gene of each of *Parageobacillus thermoglucosidasius, Geobacillus kaustophilus* and *Thermus thermophilus* and a DNA fragment containing malate/lactate dehydrogenase mldh gene of each of *Thermus thermophilus* and *Meiothermus ruber*, respectively, by PCR method. The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of *Parageobacillus thermoglucosidasius* ldh Gene (a-11)
(SEQ ID NO: 45)
5'-TTACATATGAAACAACAAGGCATGAATCGAGTAGC-3'

(b-11)
(SEQ ID NO: 46)
5'-TTAGAATTCTTATTTTACATCATCAAAATAACGGG-3'

An NdeI restriction site has been added to primer (a-11), and an EcoRI restriction site has been added to primer (b-11).

Primers for the Amplification of *Geobacillus kaustophilus* ldh Gene (a-12)
(SEQ ID NO: 47)
5'-TTACATATGAAAAACGGGAGAGGAAATCGGGTAGC-3'

(b-12)
(SEQ ID NO: 48)
5'-TTAGAATTCTTACTGAGCAAAATAGCGCGCCAATA-3'

An NdeI restriction site has been added to primer (a-12), and an EcoRI restriction site has been added to primer (b-12).

Primers for the Amplification of *Thermus thermophilus* ldh Gene (a-13)
(SEQ ID NO: 49)
5'-TTACATATGAAGGTCGGCATCGTGGGAAGCGGCAT-3'

(b-13)
(SEQ ID NO: 50)
5'-TTAGAATTCCTAAAACCCCAGGGCGAAGGCCGCCT-3'

An NdeI restriction site has been added to primer (a-13), and an EcoRI restriction site has been added to primer (b-13).

Primers for the Amplification of *Thermus thermophilus* mldh Gene (a-14)
(SEQ ID NO: 51)
5'-TTACATATGAGGTGGCGGGCGGACTTCCTCTCGGC-3'

(b-14)
(SEQ ID NO: 52)
5'-TTAGAATTCTCAAGCATCGTCCCTCCAAGGCACGC-3'

An NdeI restriction site has been added to primer (a-14), and an EcoRI restriction site has been added to primer (b-14).

Primers for the Amplification of *Meiothermus ruber* mldh-1 Gene (a-15)
(SEQ ID NO: 53)
5'-TTACATATGCAAGGCATTCCTGTGCAACAACTGCG-3'

(b-15)
(SEQ ID NO: 54)
5'-TTAGAATTCTTAAAGGCCCACCGCTTTAGCGGCCT-3'

An NdeI restriction site has been added to primer (a-15), and an EcoRI restriction site has been added to primer (b-15).

Primers for the Amplification of *Meiothermus ruber* mldh-2 Gene (a-18)
(SEQ ID NO: 55)
5'-TTACATATGAGGGTTCCTTATCCCGTACTCAAGCA-3'

(b-18)
(SEQ ID NO: 56)
5'-TTTGAATTCTCATCTTGTCCCTCCTCCTTGTAGAT-3'

An NdeI restriction site has been added to primer (a-18), and an EcoRI restriction site has been added to primer (b-18).

The produced reaction solutions were subjected to electrophoresis using a 1% agarose gel, and DNA fragments of approximately 1.0-kb were detected with regard to each of *Parageobacillus thermoglucosidasius* ldh gene, *Geobacillus kaustophilus* ldh gene, *Thermus thermophilus* ldh gene, *Thermus thermophilus* mldh gene, and *Meiothermus ruber* mldh-1 gene and mldh-2 gene.

The approximately 1.0-kb DNA fragments containing each of *Parageobacillus thermoglucosidasius* ldh gene, *Geobacillus kaustophilus* ldh gene, *Thermus thermophilus* ldh gene, *Thermus thermophilus* mldh gene, and *Meiothermus ruber* mldh-1 gene and mldh-2 gene, that were amplified by the above-described PCR, were cleaved by using restriction enzymes NdeI and EcoRI. The above-mentioned approximately 10.6-kb DNA fragment of cloning vector pCYK21 was also cleaved by using restriction enzymes NdeI and EcoRI. Each of the cleaved 1.0-kb DNA fragments and the 10.6-kb DNA fragment were linked to each other using a T4 DNA Ligase (manufactured by Takara Bio Inc.).

The obtained ligation solutions were used to transform *Hydrogenophilus thermoluteolus* strain TH-1 (NBRC 14978) by electric pulse method, and the obtained transformants were applied onto A-solid medium containing kanamycin at 50 µg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C., and plasmid DNAs were extracted from the culture solution. The plasmids, which comprise *Parageobacillus thermoglucosidasius* ldh gene, *Geobacillus kaustophilus* ldh gene, *Thermus thermophilus* ldh gene, *Thermus thermophilus* mldh gene, and *Meiothermus ruber* mldh-1 gene and mldh-2 gene, respectively, were cleaved using restriction enzymes NdeI and EcoRI, and the inserted fragments were confirmed. As a result, fragments of approximately 1.0-kb in length which were each inserted fragment of *Parageobacillus thermoglucosidasius* ldh gene, *Geobacillus kaustophilus* ldh gene, *Thermus thermophilus* ldh gene, *Thermus thermophilus* mldh gene, and *Meiothermus ruber* mldh-1 gene and mldh-2 gene, in addition to an approximately 10.6-kb DNA fragment of plasmid pCYK21 were observed.

The plasmid containing *Parageobacillus thermoglucosidasius* ldh gene was named as pC-Pth-ldh, the plasmid containing *Geobacillus kaustophilus* ldh gene was named as pC-Gka-ldh, the plasmid containing *Thermus thermophilus* ldh gene was named as pC-Tth-ldh, the plasmid containing *Thermus thermophilus* mldh gene was named as pC-Tth-mldh, the plasmid containing *Meiothermus ruber* mldh-1 gene was named as pC-Mru-mldh-1, and the plasmid containing *Meiothermus ruber* mldh-2 gene was named as pC-Mru-mldh-2.

(4-3-2) Confirmation of Expression of Lactate Dehydrogenase Gene Lactate/Malate Dehydrogenase Gene in *Hydrogenophilus thermoluteolus* Strain Each lactate dehydrogenase gene or malate/lactate dehydrogenase gene-introduced strain that was obtained as described above, was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C. for 20 hours.

Bacterial cells thus cultured and proliferated were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure lactate dehydrogenase activity by the following method. Crude enzyme solution, 50 mM sodium acetate (pH 5.0), 0.5 mM NADH, 0.2 mM fructose 1,6-bisphosphate and 5 mM sodium pyruvate were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 µmol of lactic acid per minute was defined as 1 U (Unit).

As a result, lactate dehydrogenase activity was detected in each of strain LDH03 into which *Parageobacillus thermoglucosidasius* ldh gene was introduced, strain LDH04 into which *Geobacillus kaustophilus* ldh gene was introduced, strain LDH05 into which *Thermus thermophilus* ldh gene was introduced, strain MLDH01 into which *Thermus thermophilus* mldh gene was introduced, strain MLDH02 into which *Meiothermus ruber* mldh-1 gene was introduced, and strain MLDH03 into which *Meiothermus ruber* mldh-2 gene was introduced.

TABLE 1

Lactate dehydrogenase activities of *Hydrogenophilus thermoluteolus* strains which are obtained by introducing ldh or mldh gene

| Strain | Plasmid | Introduced gene | Lactate dehydrogenase activity (U/mg-protein) |
|---|---|---|---|
| LDH03 | pC-Pth-ldh | ldh (*Parageobacillus thermoglucosidasius*) | 0.55 |
| LDH04 | pC-Gka-ldh | ldh (*Geobacillus kaustophilus*) | 0.14 |
| LDH05 | pC-Tth-ldh | ldh (*Thermus thermophilus*) | 1.21 |
| MLDH01 | pC-Tth-mldh | mldh (*Thermus thermophilus*) | 0.044 |
| MLDH02 | pC-Mru-mldh1 | mldh-1 (*Meiothermus ruber*) | 0.24 |
| MLDH03 | pC-Mru-mldh2 | mldh-2 (*Meiothermus ruber*) | 0.021 |
| pCYK21/TH-1 | pCYK21 | None | ND (Undetectable) |

The host of the transformants in Table 1 is not a lactic acid-utilizing enzyme gene-disrupted strain, but the *Hydrogenophilus thermoluteolus* TH-1 strain, which is the wild type strain. However, it was revealed that each of the above-mentioned ldh genes and mldh genes functioned in *Hydrogenophilus thermoluteolus* to enable the expression of enzymatic activity.

(4-3-3) Introduction of Lactate Dehydrogenase Gene • Malate/Lactate Dehydrogenase Gene into Lactic Acid-Utilizing Enzyme Gene-Disrupted Strain of *Hydrogenophilus* bacterium From *Hydrogenophilus thermoluteolus* LDH05 (having wild-type HPTL_1695) having the pC-Tth-ldh plasmid containing the lactate dehydrogenase gene (ldh) of *Thermus thermophilus*, and *Hydrogenophilus thermoluteolus* MLDH02 (having wild-type HPTL_1695) having the pC-Mru-mldh1 plasmid containing the malate/lactate dehydrogenase gene (mldh-1) of *Meiothermus ruber*, the respective plasmids were extracted by a conventional method, and the NOC373 strain (HPTL_1695 gene-disrupted strain) was transformed with each of the plasmids by an electric pulse method (electroporation method). The transformant was transferred to A-solid medium containing 50 µg/mL of kanamycin, and was cultured in a chamber filled with a mixed gas of $H_2:O_2:CO_2=7.5:1:1.5$ at 50° C. for 60 hours.

Each of the grown strains on the A-solid medium was inoculated into a test tube having placed therein 5 mL of A-liquid medium containing 50 µg/mL of kanamycin using a platinum loop, the test tube was filled with a mixed gas of $H_2:O_2:CO_2=7.5:1:1.5$, and shaking culture was performed at 50° C., followed by the extraction of plasmid DNA from the culture liquid. Each of the plasmids respectively containing the ldh gene of *Thermus thermophilus* and the mldh-1 gene of *Meiothermus ruber* was cleaved with restriction enzymes NdeI and EcoRI. Thus, the inserted fragments were identified. As a result, in addition to the approximately 10.6-kb DNA fragment of the plasmid pCYK21, an inserted fragment having a length of approximately 1.0-kb corresponding to each of the ldh gene of *Thermus thermophilus* and the mldh-1 gene of *Meiothermus ruber* was identified. The resultant strains were named as shown in Table 2.

TABLE 2

| Bacterial strain | Host | Plasmid | Introduced gene |
|---|---|---|---|
| LDH05 | Wild type strain | pC-Tth-ldh | ldh (*Thermus thermophilus*) |
| LAC01 | NOC373 strain (HPTL_1695 gene-disrupted strain) | pC-Tth-ldh | ldh (*Thermus thermophilus*) |
| MLDH02 | Wild type strain | pC-Mru-mldh1 | mldh-1 (*Meiothermus ruber*) |
| LAC02 | NOC373 strain (HPTL_1695 gene-disrupted strain) | pC-Mru-mldh1 | mldh-1 (*Meiothermus ruber*) |

(4-3-4) Lactic Acid Production

Each of the bacterial strains in Table 2 was inoculated into A-liquid medium containing 50 µg/ml of kanamycin using a platinum loop, and was subjected to shaking culture at 50° C. for 24 hours with a mixed gas of $H_2:O_2:CO_2=7.5:1:1.5$ being supplied along with the culture.

After the culture, lactic acid in the culture supernatant obtained by centrifugation (4° C., 15,000 rpm, 5 minutes) was quantified using F-Kit L-Lactic Acid (Roche).

As shown in Table 3, the LAC01 strain and the LAC02 strain, in each of which the HPTL_1695 gene was disrupted, showed marked increases in amount of lactic acid in the medium supernatant as compared to the corresponding LDH05 strain and MLDH02 strain, respectively.

TABLE 3

| Bacterial strain | Host | Plasmid | Introduced gene | Relative value of lactic acid concentration in medium supernatant |
|---|---|---|---|---|
| LDH05 | Wild type strain | pC-Tth-ldh | ldh (*Thermus thermophilus*) | 1 |
| LAC01 | NOC373 strain (HPTL_1695 gene-disrupted strain) | pC-Tth-ldh | ldh (*Thermus thermophilus*) | 103 |
| MLDH02 | Wild type strain | pC-Mru-mldh1 | mldh-1 (*Meiothermus ruber*) | 0.2 |
| LAC02 | NOC373 strain (HPTL_1695 gene-disrupted strain) | pC-Mru-mldh1 | mldh-1 (*Meiothermus ruber*) | 29 |

The host of the LDH05 strain and the MLDH02 strain is the *Hydrogenophilus thermoluteolus* TH-1 strain, whereas the host of the LAC01 strain and the LAC02 strain is the NOC373 strain obtained by disrupting the HPTL_1695 gene in the streptomycin-resistant strain NOC269 strain of the *Hydrogenophilus thermoluteolus* TH-1 strain.

The amount of lactic acid in the medium supernatant of a transformant was nearly the same as that of the LDH05 strain, the transformant being prepared by introducing the ldh gene of *Thermus thermophilus* to the NOC269 strain (streptomycin-resistant strain) which is the parental strain of the NOC373 strain, as a host. The amount of lactic acid in the medium supernatant of a transformant was nearly the same as that of the MLDH02 strain, the transformant being prepared by introducing the mldh-1 gene of *Meiothermus ruber* to the NOC269 strain (streptomycin-resistant strain) which is the parental strain of the NOC373 strain, as a host.

It was shown that the trait of streptomycin resistance does not affect the lactic acid-producing ability.

(5) Introduction of Lactate Permease Gene

In order to further promote the secretion of lactic acid produced in cells to the medium supernatant, a lactate permease gene was co-expressed.

(5-1) Cloning of Lactate Permease Gene

Through use of the genomic DNA of *Geobacillus kaustophilus* as a template, the lactate permease gene of *Geobacillus kaustophilus* was amplified by a PCR method. The following primers were used for the PCR. The PCR was performed by a conventional method using "DNA Thermal Cycler" manufactured by Life Technologies Corporation and using KOD FX Neo (manufactured by Toyobo Co., Ltd.) as a reaction reagent.

Primers for Amplifying Lactate Permease Gene (lutP) of *Geobacillus kaustophilus*

```
(a-19)
                              (SEQ ID NO: 57)
5'-CGGCAATTGCGGGCACAAAGGGGAGGAGAAAACCG-3'

(b-19)
                              (SEQ ID NO: 58)
5'-CGGCAATTGTTATGGAATCATCCACGACAATACCG-3'
```

The primers (a-19) and (b-19) each have an MunI restriction enzyme site added thereto.

The reaction mixture from the PCR was subjected to electrophoresis using 1% agarose gel. As a result, an approximately 1.7-kbp DNA fragment was detected for the lactate permease gene.

The approximately 1.7-kb DNA fragment containing the lactate permease gene of *Geobacillus kaustophilus* amplified by the PCR was cleaved with the restriction enzyme MunI, and cleaved with the restriction enzyme EcoRI. The DNA fragment was ligated to each of the plasmid DNAs described in (4-3-1), i.e., pC-Tth-ldh (containing the lactate dehydrogenase gene (ldh gene) of *Thermus thermophilus*) and pC-Mru-mldh1 (containing the malate/lactate dehydrogenase gene (mldh gene) of *Meiothermus ruber*) through use of T4 DNA Ligase (manufactured by Takara Bio Inc.).

The NOC269 strain and the NOC373 strain were each transformed with each resultant ligation product by an electric pulse method (electroporation method). The transformant was applied to A-solid medium containing 50 µg/mL of kanamycin, and was cultured in a chamber filled with a mixed gas of $H_2:O_2:CO_2=7.5:1:1.5$ at 50° C. for 60 hours.

From the grown strains on the solid medium, a strain having the lactate permease gene cloned downstream of the ldh gene or the mldh gene, which had been included in the plasmid, in the same direction as the ldh gene or the mldh gene was selected by colony PCR. When the colony PCR is performed using a primer corresponding to the upstream sequence of the ldh gene or the mldh gene in combination with the above-mentioned primer (b-19), a strain having the lactate permease gene cloned in the same direction as the ldh gene or the mldh gene can be identified on the basis of whether or not a DNA fragment can be amplified. The PCR was performed by a conventional method using "DNA Thermal Cycler" manufactured by Life Technologies Corporation and using TaKaRa Ex Taq (manufactured by Takara Bio Inc.) as a reaction reagent.

Primers for Colony PCR
Lactate Permease Gene lutP of *Geobacillus kaustophilus*

```
(a-20)
                                          (SEQ ID NO: 59)
5'-GGCTCGTATAATGTGTGGAATTGTGAGCGGATAAC-3'

(b-20)
                                          (SEQ ID NO: 60)
5'-CGGCAATTGTTATGGAATCATCCACGACAATACCG-3'
```

As a result, in each of the transformations, an approximately 2.7-kb DNA fragment to be amplified in the case where the lactate permease gene was cloned in the same direction as the ldh gene or the mldh gene was detected. The resultant plasmids and bacterial strains were named as shown in Table 4.

TABLE 4

| Bacterial strain | Host | Plasmid | Lactate dehydrogenase or malate/lactate dehydrogenase gene | Lactate permease gene |
|---|---|---|---|---|
| LDH05 | Wild type strain | pC-Tth-ldh | ldh (*Thermus thermophilus*) | None |
| LAC03 | NOC269 strain | pC-Tth-ldh&Gka-lutP | ldh (*Thermus thermophilus*) | lutP (*Geobacillus kaustophilus*) |
| LAC01 | NOC373 strain | pC-Tth-ldh | ldh (*Thermus thermophilus*) | None |
| LAC06 | NOC373 strain | pC-Tth-ldh&Gka-lutP | ldh (*Thermus thermophilus*) | lutP (*Geobacillus kaustophilus*) |
| MLDH02 | Wild type strain | pC-Mru-mldh1 | mldh-1 (*Meiothermus ruber*) | None |
| LAC09 | NOC269 strain | pC-Mru-mldh1&Gka-lutP | mldh-1 (*Meiothermus ruber*) | lutP (*Geobacillus kaustophilus*) |
| LAC02 | NOC373 strain | pC-Mru-mldh1 | mldh-1 (*Meiothermus ruber*) | None |
| LAC12 | NOC373 strain | pC-Mru-mldh1&Gka-lutP | mldh-1 (*Meiothermus ruber*) | lutP (*Geobacillus kaustophilus*) |

(5-2) Lactic Acid Production

Each of the strains in Table 4 having the lactate permease gene introduced thereinto was inoculated into A-liquid medium containing 50 μg/ml of kanamycin using a platinum loop, and was subjected to shaking culture at 50° C. for 24 hours with a mixed gas of $H_2:O_2:CO_2=7.5:1:1.5$ being supplied along with the culture.

After the culture, lactic acid in the culture supernatant obtained by centrifugation (4° C., 15,000 rpm, 5 minutes) was quantified using F-Kit L-Lactic Acid (Roche). As a result, it was ascertained that, as shown in Table 5, the LAC06 and LAC12 strains obtained by introducing the lactate permease gene lutP of *Geobacillus kaustophilus* into the NOC373 strain, which was an HPTL_1695 gene-disrupted strain, showed increases in amount of lactic acid in the medium supernatant as compared to the LAC01 and LAC02 strains, each of which was a strain having no lactate permease gene introduced thereinto, respectively.

When the NOC269 strain, in which the lactic acid-utilizing enzyme gene was not disrupted, was the host, the effect of the introduction of the lactate permease gene was not remarkable. In contrast, when the lactic acid-utilizing enzyme gene was disrupted, the enhancement of the lactic acid-producing ability by the introduction of the lactate permease gene became remarkable. That is, the disruption of the lactic acid-utilizing enzyme gene and the introduction of the lactate permease gene synergistically acted to enhance the lactic acid-producing ability.

TABLE 5

| Bacterial strain | Host | Plasmid | Introduced gene | Relative value of lactic acid concentration in medium supernatant |
|---|---|---|---|---|
| LDH05 | Wild type strain | pC-Tth-ldh | ldh (*Thermus thermophilus*) | 1 |
| LAC03 | NOC269 strain | pC-Tth-ldh&Gka-lutP | ldh (*Thermus thermophilus*) lutP (*Geobacillus kaustophilus*) | 1.1 |
| LAC01 | NOC373 strain | pC-Tth-ldh | ldh (*Thermus thermophilus*) | 103 |
| LAC06 | NOC373 strain | pC-Tth-ldh&Gka-lutP | ldh (*Thermus thermophilus*) lutP (*Geobacillus kaustophilus*) | 129 |
| MLDH02 | Wild type strain | pC-Mru-mldh1 | mldh-1 (*Meiothermus ruber*) | 0.2 |
| LAC09 | NOC269 strain | pC-Mru-mldh1&Gka-lutP | mldh-1 (*Meiothermus ruber*) lutP (*Geobacillus kaustophilus*) | 0.2 |
| LAC02 | NOC373 strain | pC-Mru-mldh1 | mldh-1 (*Meiothermus ruber*) | 29 |
| LAC12 | NOC373 strain | pC-Mru-mldh1&Gka-lutP | mldh-1 (*Meiothermus ruber*) lutP (*Geobacillus kaustophilus*) | 41 |

(7) Deposited Strains

*Hydrogenophilus thermoluteolus* LAC06 strain and *Hydrogenophilus thermoluteolus* LAC12 strain were deposited to NITE Patent Microorganisms Depositary, National Institute of Technology and Evaluation (2-5-8 Kazusakamatari, Kisarazu-shi, Chiba, Japan (postal code 292-0818)).

For *Hydrogenophilus thermoluteolus* LAC06 strain, the accession number is BP-03007 and the date of acceptance is Jul. 30, 2019. For *Hydrogenophilus thermoluteolus* LAC12 strain, the accession number is BP-03008 and the date of acceptance is Jul. 30, 2019.

Further, *Hydrogenophilus thermoluteolus* LDH05 strain and *Hydrogenophilus thermoluteolus* MLDH02 strain are also deposited to NITE Patent Microorganisms Depositary, National Institute of Technology and Evaluation (2-5-8 Kazusakamatari, Kisarazu-shi, Chiba, Japan (postal code 292-0818)).

For *Hydrogenophilus thermoluteolus* LDH05 strain, the accession number is BP-02822 and the date of acceptance is Nov. 14, 2018. For *Hydrogenophilus thermoluteolus* MLDH02 strain, the accession number is BP-02828 and the date of acceptance is Nov. 21, 2018.

Therefore, these strains are available to the general public.

Furthermore, all strains (including ATCC strains and NBRC strains) that are described in the present specification are internationally deposited under the Budapest Treaty, or are possessed by organizations that furnish the strains without any terms or conditions, or are marketed, and therefore, these strains are all available to the general public.

INDUSTRIAL APPLICABILITY

The recombinant of the present invention effectively produces lactic acid using carbon dioxide as a sole carbon source, and therefore, it is able to efficiently produce the material of biodegradable plastics, while solving global warming caused by increased emissions of carbon dioxide.

The invention claimed is:

1. A recombinant *Hydrogenophilus* bacterium, which has a lactate dehydrogenase gene introduced thereinto, and in which one or more of three lactic acid-utilizing enzyme genes (a), (b), and (c) on a genome are disrupted so that lactic acid production in the bacterium is increased, wherein the lactic acid-utilizing enzyme gene (a) comprises at least one selected from the group consisting of:

DNA comprising a nucleotide sequence having 90% or more identity to SEQ ID NO: 1;

DNA encoding a polypeptide comprising an amino acid sequence having 90% or more identity to SEQ ID NO: 2; and DNA encoding a polypeptide comprising an amino acid sequence having deletion, substitution, or addition of one to five of amino acids in the amino acid sequence of SEQ ID NO: 2;

wherein the lactic acid-utilizing enzyme gene (b) comprises at least one selected from the group consisting of:

DNA comprising a nucleotide sequence having 90% or more identity to SEQ ID NO: 3, DNA encoding a polypeptide comprising an amino acid sequence having 90% or more identity to SEQ ID NO: 4; and DNA encoding a polypeptide comprising an amino acid sequence having deletion, substitution, or addition of 1 to 5 of amino acids in the amino acid sequence of SEQ ID NO: 4; and wherein the lactic acid-utilizing enzyme gene (c) comprises at least one selected from the group consisting of:

DNA comprising a nucleotide sequence having 90% or more identity to SEQ ID NO: 5;

DNA encoding a polypeptide comprising an amino acid sequence having 90% or more identity to SEQ ID NO: 6; and DNA encoding a polypeptide comprising an amino acid sequence having deletion, substitution, or addition of 1 to 5 of amino acids in the amino acid sequence of SEQ ID NO: 6.

2. The recombinant *Hydrogenophilus* bacterium according to claim 1, wherein the one or more of three lactic acid-utilizing enzyme genes are disrupted by introducing a deletion, an addition, a substitution, or a combination thereof, of one or a plurality of nucleotides into the one or more of three lactic acid-utilizing enzyme genes.

3. The recombinant *Hydrogenophilus* bacterium according to claim 1, wherein the lactate dehydrogenase gene comprises at least one selected from the group consisting of:

DNA comprising a nucleotide sequence having 90% or more identity to SEQ ID NO: 9, 10, or 11;

DNA encoding a polypeptide comprising an amino acid sequence having 90% or more identity to SEQ ID NO: 12, 13, or 14; and DNA encoding a polypeptide comprising an amino acid sequence having deletion, substitution, or addition of one to five of amino acids in the amino acid sequence of SEQ ID NO: 12, 13, or 14.

4. The recombina*nt Hydrogenophil*us bacterium according to claim 1, wherein the recombina*nt Hydrogenophil*us bacterium further comprises a lactate permease gene introduced thereinto.

5. The recombinant *Hydrogenophilus* bacterium according to claim 4, wherein the lactate permease gene comprises at least one selected from the group consisting of:

DNA comprising a nucleotide sequence having 90% or more identity to SEQ ID NO: 21;

DNA encoding a polypeptide comprising an amino acid sequence having 90% or more identity to SEQ ID NO: 22; and DNA encoding a polypeptide comprising an amino acid sequence having deletion, substitution, or addition of one to five of amino acids in the amino acid sequence of SEQ ID NO: 22.

6. A method of producing lactic acid, comprising a step of culturing the recombinant *Hydrogenophilus* bacterium of claim 1 through use of carbon dioxide as a substantially sole carbon source.

7. The recombinant *Hydrogenophilus* bacterium according to claim 1, which a malate/lactate dehydrogenase gene is introduced thereinto.

8. The recombinant *Hydrogenophilus* bacterium according to claim 7, wherein the malate/lactate dehydrogenase gene comprises DNA at least one selected from the group consisting of:

DNA comprising a nucleotide sequence having 90% or more identity to SEQ ID NO: 15, 16, or 17, DNA encoding a polypeptide comprising an amino acid sequence having 90% or more identity to SEQ ID NO: 18, 19, or 20, and DNA encoding a polypeptide comprising an amino acid sequence having deletion, substitution, or addition of one to five of amino acids in the amino acid sequence of SEQ ID NO: 18, 19, or 20.

9. A recombinant *Hydrogenophilus* bacterium, which has a malate/lactate dehydrogenase gene introduced thereinto, and in which one or more of three lactic acid-utilizing enzyme genes (a), (b), and (c) on a genome are disrupted so that lactic acid production in the bacterium is increased, wherein the lactic acid-utilizing enzyme gene (a) comprises at least one selected from the group consisting of:

DNA comprising a nucleotide sequence having 90% or more identity to SEQ ID NO: 1, DNA encoding a polypeptide comprising an amino acid sequence having 90% or more identity to SEQ ID NO: 2, and DNA encoding a polypeptide comprising an amino acid sequence having deletion, substitution, or addition of one to five of amino acids in the amino acid sequence of SEQ ID NO: 2, wherein lactic acid-utilizing enzyme gene (b) comprises at least one selected from the group consisting of:

DNA comprising a nucleotide sequence having 90% or more identity to SEQ ID NO: 3, DNA encoding a polypeptide comprising an amino acid sequence having 90% or more identity to SEQ ID NO: 4, and DNA encoding a polypeptide comprising an amino acid sequence having deletion, substitution, or addition of one to five of amino acids in the amino acid sequence of SEQ ID NO: 4, wherein lactic acid-utilizing enzyme gene (c) comprises at least one selected from the group consisting of:

DNA comprising a nucleotide sequence having 90% or more identity to SEQ ID NO: 5, DNA encoding a polypeptide comprising an amino acid sequence having 90% or more identity to SEQ ID NO: 6, and DNA encoding a polypeptide comprising an amino acid sequence having deletion, substitution, or addition of one to five of amino acids in the amino acid sequence of SEQ ID NO: 6.

10. The recombinant *Hydrogenophilus* bacterium according to claim 9, wherein the malate/lactate dehydrogenase gene comprises at least one selected from the group consisting of:

DNA comprising a nucleotide sequence having 90% or more identity to SEQ ID NO: 15, 16, or 17, DNA encoding a polypeptide comprising an amino acid sequence having 90% or more identity to SEQ ID NO: 18, 19, or 20, and DNA encoding a polypeptide comprising an amino acid sequence having deletion, substitution, or addition of one to five of amino acids in the amino acid sequence of SEQ ID NO: 18, 19, or 20.

11. The recombinant *Hydrogenophilus* bacterium according to claim 9, wherein the one or more of three lactic acid-utilizing enzyme genes are disrupted by introducing a deletion, an addition, a substitution, or a combination thereof, of one to 1000 of nucleotides into the one or more of three lactic acid-utilizing enzyme genes.

12. The recombinant *Hydrogenophilus* bacterium according to claim 9, wherein the recombinant *Hydrogenophilus* bacterium further has a lactate permease gene introduced thereinto.

13. The recombinant *Hydrogenophilus* bacterium according to claim 12, wherein the lactate permease gene comprises at least one selected from the group consisting of:
    DNA comprising a base sequence having 90% or more identity to SEQ ID NO: 21,
    DNA encoding a polypeptide comprising an amino acid sequence having 90% or more identity to SEQ ID NO: 22, and
    DNA encoding a polypeptide comprising an amino acid sequence having deletion, substitution, or addition of one to five of amino acids in the amino acid sequence of SEQ ID NO: 22.

14. A method of producing lactic acid, comprising culturing the recombinant *Hydrogenophilus* bacterium of claim 11 through use of carbon dioxide as a substantially sole carbon source.

15. The recombinant *Hydrogenophilus* bacterium according to claim 4, wherein a malate/lactate dehydrogenase gene is introduced thereinto.

16. The recombinant *Hydrogenophilus* bacterium according to claim 15, wherein the malate/lactate dehydrogenase gene comprises at least one selected from the group consisting of:
    DNA comprising a nucleotide sequence having 90% or more identity to SEQ ID NO: 15, 16, or 17,
    DNA encoding a polypeptide comprising an amino acid sequence having 90% or more identity to SEQ ID NO: 18, 19, or 20, and
    DNA encoding a polypeptide comprising an amino acid sequence having deletion, substitution, or addition of one to five of amino acids in the amino acid sequence of SEQ ID NO: 18, 19, or 20.

17. The recombinant *Hydrogenophilus* bacterium according to claim 1, wherein the one or more of three lactic acid-utilizing enzyme genes are disrupted by introducing a deletion, an addition, a substitution, or a combination thereof, of one to 1000 of nucleotides into the one or more of three lactic acid-utilizing enzyme genes.

\* \* \* \* \*

UNITED STATES PATENT AND TRADEMARK OFFICE
CERTIFICATE OF CORRECTION

PATENT NO. : 12,305,199 B2
APPLICATION NO. : 17/631066
DATED : May 20, 2025
INVENTOR(S) : Hideaki Yukawa et al.

It is certified that error appears in the above-identified patent and that said Letters Patent is hereby corrected as shown below:

In the Claims

In Column 81, Claim 14, Line 18, revise "claim 11" to "claim 9".

Signed and Sealed this
Fifteenth Day of July, 2025

Coke Morgan Stewart
*Acting Director of the United States Patent and Trademark Office*

SEQUENCE LISTING

<160> NUMBER OF SEQ ID NOS: 60

<210> SEQ ID NO 1
<211> LENGTH: 759
<212> TYPE: DNA
<213> ORGANISM: Hydrogenophilus thermoluteolus

<400> SEQUENCE: 1

```
atggctaccc aaccccgcgt cggtctcttt gtcacctgcc tggtcaatac catccgtccc      60
aacatcgcga tggcgcttgc acaactcttg gaagccacgg ggcaccgcgt cgaagtcccg     120
ttcgcgcaaa cctgctgcgg gcaacccggc tacaacgcgg gggactggga tgccgcccgt     180
gcgcttgcga agcagaccat cgccgcgttc gaacccttcg attatctcat cgcgccgtcg     240
ggctcgtgcc ttgcgacgat cgccacgac tatccggagc tgctcaaaga cgatcccgaa     300
tggcgggaac gcgcgcaacg gctcgcagcc aagtcgtggg aagcgctgag ctacttcgcc     360
caacaggttc cattggaaca actcccacgg gtccggttcc cctatcgcgt cacctaccac     420
gactcctgtt ccggcttgcg cagcctgggg atcaagggac aaccgcgcca gctccttgcc     480
cgtgtcgaag ggctgacgct cgtggagatg gcagaggccg aggtgtgttg cgggttcggt     540
ggcaccttct gcgtcaaata tcccgaactc tccgaggcga tggtcgaacg caaggtccaa     600
aacatcctga agagcggcgc gcaagtgctc ttaggcggcg acctgggttg tctgatgaac     660
attgccgggc ggcttgcgcg catccatgcc ccggtccggg tctatcatac cctcgaagtg     720
ctggcggggc tgcaaatgg tcccggttg aatggctga                              759
```

<210> SEQ ID NO 2
<211> LENGTH: 252
<212> TYPE: PRT
<213> ORGANISM: Hydrogenophilus thermoluteolus

<400> SEQUENCE: 2

```
Met Ala Thr Gln Pro Arg Val Gly Leu Phe Val Thr Cys Leu Val Asn
1               5                  10                  15

Thr Ile Arg Pro Asn Ile Ala Met Ala Leu Ala Gln Leu Leu Glu Ala
            20                  25                  30

Thr Gly His Arg Val Glu Val Pro Phe Ala Gln Thr Cys Cys Gly Gln
        35                  40                  45

Pro Gly Tyr Asn Ala Gly Asp Trp Asp Ala Ala Arg Ala Leu Ala Lys
    50                  55                  60

Gln Thr Ile Ala Ala Phe Glu Pro Phe Asp Tyr Leu Ile Ala Pro Ser
65                  70                  75                  80

Gly Ser Cys Leu Ala Thr Ile Arg His Asp Tyr Pro Glu Leu Leu Lys
                85                  90                  95

Asp Asp Pro Glu Trp Arg Glu Arg Ala Gln Arg Leu Ala Ala Lys Ser
            100                 105                 110

Trp Glu Ala Leu Ser Tyr Phe Ala Gln Gln Val Pro Leu Glu Gln Leu
        115                 120                 125

Pro Arg Val Arg Phe Pro Tyr Arg Val Thr Tyr His Asp Ser Cys Ser
```

```
                     130                  135                  140
Gly Leu Arg Ser Leu Gly Ile Lys Gly Gln Pro Arg Gln Leu Leu Ala
145                 150                  155                 160

Arg Val Glu Gly Leu Thr Leu Val Glu Met Ala Glu Ala Glu Val Cys
                165                  170                  175

Cys Gly Phe Gly Gly Thr Phe Cys Val Lys Tyr Pro Glu Leu Ser Glu
            180                  185                  190

Ala Met Val Glu Arg Lys Val Gln Asn Ile Leu Lys Ser Gly Ala Gln
        195                  200                  205

Val Leu Leu Gly Gly Asp Leu Gly Cys Leu Met Asn Ile Ala Gly Arg
    210                  215                  220

Leu Ala Arg Ile His Ala Pro Val Arg Val Tyr His Thr Leu Glu Val
225                 230                  235                  240

Leu Ala Gly Leu Ala Asn Gly Pro Gly Leu Asn Gly
                245                  250
```

<210> SEQ ID NO 3
<211> LENGTH: 1428
<212> TYPE: DNA
<213> ORGANISM: Hydrogenophilus thermoluteolus

<400> SEQUENCE: 3

| | | | | | |
|---|---|---|---|---|---|
| atgaccagcc | gcactccacg | ccgctttcgc | gaacaagcgg | tcttcgcgct | gcacgagccc | 60 |
| aatctccagg | cggcgctttc | ccgtgccgcg | gatggcttca | tcggcaaacg | cgcgaaagcg | 120 |
| gttgcgctcg | tccccgaatt | cgagcagttg | cgcgaagcgg | gcgcccagcg | caaagatgaa | 180 |
| atcctggcca | acctcgacac | ctacctcgcc | gcgttcgaag | cagaggtcac | ccgccacggc | 240 |
| ggtgtcgtcc | attgggcacc | cgatgccgac | gcggcgcgcc | gcatcattct | ggagatctgc | 300 |
| gccgcagcga | atgcccgcgt | gatcaccaag | ggcaaatcga | tggtctccga | ggagatcggg | 360 |
| ctcaacgagg | cgctggaggc | agcggggtac | gaaatcgtcg | aaaccgacct | aggggagtac | 420 |
| atcattcagc | tggcgggaga | agctccttca | cacatcatcg | cccccgcggt | ccacaaaacc | 480 |
| aaagagcaga | tctccgacct | cttcgaagcc | gcgcatggca | cgccgcggca | acgaccgtc | 540 |
| gaagggctgg | tcaccgaggc | gcggttgcag | ctgcgacaaa | agtacttcca | gcagacgtc | 600 |
| ggcatcaccg | gcgcgaactt | cctcgtagcc | gagacgggac | agaccctcat | cgtcaccaac | 660 |
| gaagggaacg | gtgacctcac | gcagacgctc | gcacgggtcc | atatcgtcac | cgccggaatc | 720 |
| gagcgggtgg | tcggcaccct | cgaggacgtt | gcgctctttc | tgcgtttgct | cgcgcgttcc | 780 |
| gcaacggggc | aagacagcga | aacctacacc | acctactccg | tcggcccgca | ccgcgcaggc | 840 |
| gaccaggacg | gcccggaagc | gtttcacgtc | gtgctcgtcg | acaacggacg | cagccggatg | 900 |
| ctcgatggac | cgttccgtcc | aatgttgcgc | tgcatccgct | gcggcgcgtg | catgaaccat | 960 |
| tgcccggtct | atggcgcgat | cggcgggcat | gcgtacggtt | gggtctaccc | ggggccgatg | 1020 |
| ggatcggtct | tgactccgct | ctttaccgga | ctcgacaacg | cgctcgatct | gcccaacgcc | 1080 |
| tgcacgctga | acggtcgttg | cggtgaagtg | tgcccggtga | aaatcccatt | gccggacctg | 1140 |
| ctgcgccgtc | ttcgccacga | acagcacaaa | gcgggccttc | gtccggcgct | ggaaggacgg | 1200 |
| gccctcaccc | tctggcgctg | gctcgcaacc | cgccctgcgc | tctaccatgc | gcggaacgg | 1260 |
| gtcaaagtca | ggctgctcgc | cgcgtgggcg | cgcgggcgca | agacgcttga | ctggtttccc | 1320 |
| ttcgcccgcg | gctggtttgg | ggttcgtgac | ctgcccacgc | ccccgggacg | caccttctc | 1380 |
| gaactgtggc | acgccaaacg | cgaaaaccca | aacggaggcg | agcgatga | | 1428 |

<210> SEQ ID NO 4
<211> LENGTH: 475
<212> TYPE: PRT
<213> ORGANISM: Hydrogenophilus thermoluteolus

<400> SEQUENCE: 4

```
Met Thr Ser Arg Thr Pro Arg Arg Phe Arg Glu Gln Ala Val Phe Ala
1               5                   10                  15

Leu His Glu Pro Asn Leu Gln Ala Ala Leu Ser Arg Ala Ala Asp Gly
            20                  25                  30

Phe Ile Gly Lys Arg Ala Lys Ala Val Ala Leu Val Pro Glu Phe Glu
        35                  40                  45

Gln Leu Arg Glu Ala Gly Ala Gln Arg Lys Asp Glu Ile Leu Ala Asn
50                  55                  60

Leu Asp Thr Tyr Leu Ala Ala Phe Glu Ala Val Thr Arg His Gly
65                  70                  75                  80

Gly Val Val His Trp Ala Pro Asp Ala Asp Ala Ala Arg Arg Ile Ile
                85                  90                  95

Leu Glu Ile Cys Ala Ala Ala Asn Ala Arg Val Ile Thr Lys Gly Lys
            100                 105                 110

Ser Met Val Ser Glu Glu Ile Gly Leu Asn Glu Ala Leu Glu Ala Ala
        115                 120                 125

Gly Tyr Glu Ile Val Glu Thr Asp Leu Gly Glu Tyr Ile Ile Gln Leu
130                 135                 140

Ala Gly Glu Ala Pro Ser His Ile Ile Ala Pro Ala Val His Lys Thr
145                 150                 155                 160

Lys Glu Gln Ile Ser Asp Leu Phe Glu Ala Ala His Gly Thr Pro Arg
                165                 170                 175

Gln Thr Thr Val Glu Gly Leu Val Thr Glu Ala Arg Leu Gln Leu Arg
            180                 185                 190

Gln Lys Tyr Phe Gln Ala Asp Val Gly Ile Thr Gly Ala Asn Phe Leu
        195                 200                 205

Val Ala Glu Thr Gly Gln Thr Leu Ile Val Thr Asn Glu Gly Asn Gly
210                 215                 220

Asp Leu Thr Gln Thr Leu Ala Arg Val His Ile Val Thr Ala Gly Ile
225                 230                 235                 240

Glu Arg Val Val Gly Thr Leu Glu Asp Val Ala Leu Phe Leu Arg Leu
                245                 250                 255

Leu Ala Arg Ser Ala Thr Gly Gln Asp Ser Glu Thr Tyr Thr Thr Tyr
            260                 265                 270

Ser Val Gly Pro His Arg Ala Gly Asp Gln Asp Gly Pro Glu Ala Phe
        275                 280                 285

His Val Val Leu Val Asp Asn Gly Arg Ser Arg Met Leu Asp Gly Pro
290                 295                 300

Phe Arg Pro Met Leu Arg Cys Ile Arg Cys Gly Ala Cys Met Asn His
305                 310                 315                 320

Cys Pro Val Tyr Gly Ala Ile Gly Gly His Ala Tyr Gly Trp Val Tyr
                325                 330                 335

Pro Gly Pro Met Gly Ser Val Leu Thr Pro Leu Phe Thr Gly Leu Asp
            340                 345                 350

Asn Ala Leu Asp Leu Pro Asn Ala Cys Thr Leu Asn Gly Arg Cys Gly
        355                 360                 365

Glu Val Cys Pro Val Lys Ile Pro Leu Pro Asp Leu Leu Arg Arg Leu
370                 375                 380
```

```
Arg His Glu Gln His Lys Ala Gly Leu Arg Pro Ala Leu Glu Gly Arg
385                 390                 395                 400

Ala Leu Thr Leu Trp Arg Trp Leu Ala Thr Arg Pro Ala Leu Tyr His
            405                 410                 415

Ala Ala Glu Arg Val Lys Val Arg Leu Leu Ala Ala Trp Ala Arg Gly
        420                 425                 430

Arg Lys Thr Leu Asp Trp Phe Pro Phe Ala Arg Gly Trp Phe Gly Val
    435                 440                 445

Arg Asp Leu Pro Thr Pro Pro Gly Arg Thr Phe Leu Glu Leu Trp His
450                 455                 460

Ala Lys Arg Glu Asn Pro Asn Gly Gly Glu Arg
465                 470                 475

<210> SEQ ID NO 5
<211> LENGTH: 756
<212> TYPE: DNA
<213> ORGANISM: Hydrogenophilus thermoluteolus

<400> SEQUENCE: 5
atgaacgcaa ccgcaggctt tcccacgtcg caacgacccg aacggctgga ctccgcttcg      60
acaaacgaca gcaccgccac ccggcacgcc gacggtcgtg aacgggtgct cgctgcgatc     120
cgcgctgcgc tgggcaaaaa tggcgcagtt gagcctgccg atcccgctgc gcgtgccgct     180
gcgatcaccc cgcgcgcacc ccaccccggg ctggcgttct ctgaaccagt cgcggcacga     240
tggcaacgac tttggaccgc acgtgccgga acggtgcacg aactcccttc cgcgacgcc     300 cttcccgaag cggtcgcggc gtggtgtgcc gaagtgggtg ccacaccgcc cacacacgcg     360
agcggcaccc tcctcgacct cccctggcct gctgcgtggc aactgcgctg cgaaccggca     420
accgtcacca cggaaaccgc ggtgagcgaa gcgtacgctg catcgccga agtgggaagt     480 cttgtcttcc tctccgcccc cgtgcatccc accaccacc ggttcgtgcc agacaaccac     540
ctcgtgctgc tatcgcagtc ccgcatcgtt tcccatttcg aggagttctg ggcgctgctg     600
cgccgcgaac tgggtgacga cacaaccgat tggcgcgaac atctgccgcg caccatcaac     660
ttcgtcgctg gcccctcacg caccggagac gtcgagcaga cgatccagtt gggcgcccat     720
gggccgcggc gggtgcacgt cttcttgatc ccctga                              756

<210> SEQ ID NO 6
<211> LENGTH: 251
<212> TYPE: PRT
<213> ORGANISM: Hydrogenophilus thermoluteolus

<400> SEQUENCE: 6

Met Asn Ala Thr Ala Gly Phe Pro Thr Ser Gln Arg Pro Glu Arg Leu
1               5                   10                  15

Asp Ser Ala Ser Thr Asn Asp Ser Thr Ala Thr Arg His Ala Asp Gly
            20                  25                  30

Arg Glu Arg Val Leu Ala Ala Ile Arg Ala Ala Leu Gly Lys Asn Gly
        35                  40                  45

Ala Val Glu Pro Ala Asp Pro Ala Ala Arg Ala Ala Ile Thr Pro
    50                  55                  60

Arg Ala Pro His Pro Arg Leu Ala Phe Ser Glu Pro Val Ala Ala Arg
65                  70                  75                  80

Trp Gln Arg Leu Trp Thr Ala Arg Ala Gly Thr Val His Glu Leu Pro
                85                  90                  95
```

Ser Arg Asp Ala Leu Pro Glu Ala Val Ala Ala Trp Cys Ala Glu Val
           100                 105                 110

Gly Ala Thr Pro Pro Thr His Ala Ser Gly Thr Leu Leu Asp Leu Pro
       115                 120                 125

Trp Pro Ala Ala Trp Gln Leu Arg Cys Glu Pro Ala Thr Val Thr Thr
130                 135                 140

Glu Thr Ala Val Ser Glu Ala Tyr Ala Gly Ile Ala Glu Val Gly Ser
145                 150                 155                 160

Leu Val Phe Leu Ser Ala Pro Val His Pro Thr His Arg Phe Val
               165                 170                 175

Pro Asp Asn His Leu Val Leu Leu Ser Gln Ser Arg Ile Val Ser His
           180                 185                 190

Phe Glu Glu Phe Trp Ala Leu Leu Arg Arg Glu Leu Gly Asp Asp Thr
       195                 200                 205

Thr Asp Trp Arg Glu His Leu Pro Arg Thr Ile Asn Phe Val Ala Gly
210                 215                 220

Pro Ser Arg Thr Gly Asp Val Glu Gln Thr Ile Gln Leu Gly Ala His
225                 230                 235                 240

Gly Pro Arg Arg Val His Val Phe Leu Ile Pro
               245                 250

<210> SEQ ID NO 7
<211> LENGTH: 396
<212> TYPE: DNA
<213> ORGANISM: Hydrogenophilus thermoluteolus

<400> SEQUENCE: 7
atgccaacca tcaaccagtt ggtgcgtcgt ccgcggaaaa cggcgcccga aaagagcaaa      60
gtgccggcgt tgcagggatg tccgcaaaaa cgaggcgtgt gtacgcgcgt ctataccacg     120
acgccgaaaa agccgaactc ggcccttcgt aaggtcgcga agtgcgtttt gaccaacggt     180
tacgaggtga tttcgtacat cggcggcgaa gggcacaatc tgcaagaaca ctcggtggtg     240
ctgattcgtg gcggccgggt gaaagacctg ccgggtgtgc gttaccacat cgtgcgcggt     300
tcgctcgact gcaagggggt caaggaccgt aagcaagggc gttccaagta cggggcgaag     360
cgtccgaagc cgggcgccgc tgcgggcaag aaataa                               396

<210> SEQ ID NO 8
<211> LENGTH: 1026
<212> TYPE: DNA
<213> ORGANISM: Escherichia coli

<400> SEQUENCE: 8
atgaaaaagc tgaactcac cgcgacatct gtcgagaagt ttctgatcga aaagttcgac       60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg gcccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600

```
tccaacaatg tcctgacgga caatggccgc ataacagcgg tcattgactg gagcgaggcg        660
atgttcgggg attcccaata cgaggtcgcc aacatcttct tctggaggcc gtggttggct        720
tgtatggagc agcagacgcg ctacttcgag cggaggcatc cggagcttgc aggatcgccg        780
cggctccggg cgtatatgct ccgcattggt cttgaccaac tctatcagag cttggttgac        840
ggcaatttcg atgatgcagc ttgggcgcag ggtcgatgcg acgcaatcgt ccgatccgga        900
gccgggactg tcgggcgtac acaaatcgcc cgcagaagcg cggccgtctg gaccgatggc        960
tgtgtagaag tactcgccga tagtggaaac cgacgcccca gcactcgtcc gagggcaaag       1020
gaatag                                                                  1026

<210> SEQ ID NO 9
<211> LENGTH: 960
<212> TYPE: DNA
<213> ORGANISM: Parageobacillus thermoglucosidasius

<400> SEQUENCE: 9
atgaaacaac aaggcatgaa tcgagtagca cttataggaa cggggttcgt tggggccagc         60
tatgcatttg cccttatgaa ccaaggaata gcagatgagt tagtattgat tgatgtaaat        120
aagaataagg cagagggcga tgtgatggat ttaaatcacg gaaaagtatt cgcgccgaag        180
ccgatgaata tttggtttgg agattatcaa gattgccaag acgccgattt ggtggtgatt        240
tgtgcagggg ctaaccaaaa gccgggagaa acaagactgg atcttgttga caaaaatatt        300
aatatcttca aaacgattgt cgattctgtg atgaaatccg gatttgatgg cgttttctct        360
gtggcaacga acccagtgga tattttaacg tatgctactt ggaaatttag cgggttaccg        420
aaagagcggg taatcggctc aggaacgatt cttgatacag caagattccg cttcttgcta        480
agtgaatatt ttcaagtggc tccgaccaat gtacatgcgt atattattgg cgagcatggg        540
gatacagagc tgcctgtttg gagccatgcg gaaattggaa gcattccagt tgagcaaata        600
ttgatgcaaa acgataacta tagaaaagag gatttagaca atatctttgt taatgttcgt        660
gatgcggcat atcaaatcat tgagaaaaaa ggggcaacgt attacggcat tgcaatggga        720
ttagtccgta tcactcgtgc tatttttgcac aatgaaaatg ccatcttaac cgtttctgct        780
catttggacg ccaatatgg cgaacgaaat gtttatattg gcgtgcctgc cattatcaac        840
cgaaacggta ttcgtgaagt gatggaattg acgctaaatg aaacagaaca acaacaattc        900
catcatagtg taactgtatt aaaagacatt cttttcccgtt attttgatga tgtaaaataa        960

<210> SEQ ID NO 10
<211> LENGTH: 954
<212> TYPE: DNA
<213> ORGANISM: Geobacillus kaustophilus

<400> SEQUENCE: 10
atgaaaaacg ggagaggaaa tcgggtagcg gtcgtcggca ccgggtttgt cggcgccagt         60
tatgcgtttg ccttaatgaa tcaagggatt gccgatgaga tcgtgctcat cgatgcaaat        120
gaaaacaagg ctgagggcga tgcgatggac ttcaaccatg ggaaagtatt tgcgccgaag        180
ccggctgaca tttggcacgg cgattacgat gattgccgcg atgccgattt ggttgtcatt        240
tgcgccggcg ccaaccaaaa accgggcgag acgcggcttg atcttgtgga caaaaacatt        300
gccattttcc gctcgatcgt tgagtcggtc atggcatccg gatttcaagg actgtttctc        360
gtcgccacca atccggtcga catttttaacg tacgcgacgt ggaaattcag cggcctgccg        420
```

```
caagagcgag taatcggatc gggcacgatt ttggacacgg cgcggttccg cttcttgttg    480
ggcgactatt tcgccgtcgc cccgacgaac gtgcacgcct atattatcgg cgaacatggc    540
gacactgaac tcccggtctg agccaggct gatatcggcg gcgtgccgat ccgcaagctg     600
gtcgagtcta aagggaaga agcgcaaaaa gagctcgagc gcattttgt caatgtgcgc      660
gatgccgcct accaaattat tgagaaaaaa ggagcgacgt actacgggat tgctatgggg    720
cttgcccgcg tgacgcgcgc cattttgcat catgaaaatg ccattttgac cgtttccgct    780
tacttggacg gcccatacgg cgaacgcgat gtctacatcg gtgtgcctgc tgtgatcaac    840
cgaaatggca tccgcgaagt gattgaaatt gaacttgacg aggaggagaa aaaatggttc    900
caccgtagtg ctgcgacgtt aaaaggtgta ttggcgcgct attttgctca gtaa          954

<210> SEQ ID NO 11
<211> LENGTH: 933
<212> TYPE: DNA
<213> ORGANISM: Thermus thermophilus

<400> SEQUENCE: 11
atgaaggtcg gcatcgtggg aagcggcatg gtggggagcg ccaccgccta cgccctggcc    60
ctcctcggcg tggcgcggga ggtggtcctc gtggacctgg accggaagct ggcccaggcc   120
cacgccgagg acatcctcca cgccacgccc ttcgccacc cggtctgggt gcgggcgggg   180
tcgtacgggg acctcgaggg ggcccggcg gtggtgctcg ccgccggggt ggcccagcgc   240
cccggggaga cccgcctgca gcttctggac cgcaacgccc aggtcttcgc ccaggtggtg   300
ccccgggttt tagaggcggc cccggaggcg gtgctcctcg tggccacgaa cccggtggac   360
gtgatgaccc aggtggccta ccgcctctcc ggcctgcccc cggggcgggt ggtgggctcg   420
gggacgatcc tggacacggc ccgcttccgg gcccttctgg cggagtacct ccgggtggcc   480
ccccagtcgg tccacgccta cgtgctgggg gagcacgggg actcggaggt gctggtctgg   540
tccagcgccc aggtgggcgg ggtgcccctc ctggagttcg ccgaggcccg ggggcgggcc   600
cttccccgg aggaccgggc ccgcattgac gaaggggtcc gccgggccgc ctaccggatc   660
attgaggga aggggccac ctactacggc atcgggcgg cctcgcccg gcttgtgcgg   720
gccatcctca ccgacgaaaa gggggtgtac accgtgagcg ccttcacccc cgaggtggag   780
ggggtcttgg aggtgagcct ctccctgccc cgcatcctgg gcgcggggg cgtgagggg    840
accgtctacc gagcctgag cccggaggag cggaggcct tgcggcggag cgccgagatc   900
ctcaaggagg cggccttcgc cctggggttt tag                                933

<210> SEQ ID NO 12
<211> LENGTH: 319
<212> TYPE: PRT
<213> ORGANISM: Parageobacillus thermoglucosidasius

<400> SEQUENCE: 12

Met Lys Gln Gln Gly Met Asn Arg Val Ala Leu Ile Gly Thr Gly Phe
1               5                   10                  15

Val Gly Ala Ser Tyr Ala Phe Ala Leu Met Asn Gln Gly Ile Ala Asp
                20                  25                  30

Glu Leu Val Leu Ile Asp Val Asn Lys Asn Lys Ala Glu Gly Asp Val
            35                  40                  45

Met Asp Leu Asn His Gly Lys Val Phe Ala Pro Lys Pro Met Asn Ile
        50                  55                  60

Trp Phe Gly Asp Tyr Gln Asp Cys Gln Asp Ala Asp Leu Val Val Ile
```

```
                65                  70                  75                  80
        Cys Ala Gly Ala Asn Gln Lys Pro Gly Glu Thr Arg Leu Asp Leu Val
                            85                  90                  95

Asp Lys Asn Ile Asn Ile Phe Lys Thr Ile Val Asp Ser Val Met Lys
                        100                 105                 110

Ser Gly Phe Asp Gly Val Phe Leu Val Ala Thr Asn Pro Val Asp Ile
                    115                 120                 125

Leu Thr Tyr Ala Thr Trp Lys Phe Ser Gly Leu Pro Lys Glu Arg Val
                130                 135                 140

Ile Gly Ser Gly Thr Ile Leu Asp Thr Ala Arg Phe Arg Phe Leu Leu
        145                 150                 155                 160

Ser Glu Tyr Phe Gln Val Ala Pro Thr Asn Val His Ala Tyr Ile Ile
                        165                 170                 175

Gly Glu His Gly Asp Thr Glu Leu Pro Val Trp Ser His Ala Glu Ile
                    180                 185                 190

Gly Ser Ile Pro Val Glu Gln Ile Leu Met Gln Asn Asp Asn Tyr Arg
                195                 200                 205

Lys Glu Asp Leu Asp Asn Ile Phe Val Asn Val Arg Asp Ala Ala Tyr
                210                 215                 220

Gln Ile Ile Glu Lys Lys Gly Ala Thr Tyr Tyr Gly Ile Ala Met Gly
        225                 230                 235                 240

Leu Val Arg Ile Thr Arg Ala Ile Leu His Asn Glu Asn Ala Ile Leu
                        245                 250                 255

Thr Val Ser Ala His Leu Asp Gly Gln Tyr Gly Glu Arg Asn Val Tyr
                    260                 265                 270

Ile Gly Val Pro Ala Ile Ile Asn Arg Asn Gly Ile Arg Glu Val Met
                275                 280                 285

Glu Leu Thr Leu Asn Glu Thr Glu Gln Gln Gln Phe His His Ser Val
                290                 295                 300

Thr Val Leu Lys Asp Ile Leu Ser Arg Tyr Phe Asp Asp Val Lys
        305                 310                 315

<210> SEQ ID NO 13
<211> LENGTH: 317
<212> TYPE: PRT
<213> ORGANISM: Geobacillus kaustophilus

<400> SEQUENCE: 13

Met Lys Asn Gly Arg Gly Asn Arg Val Ala Val Val Gly Thr Gly Phe
        1               5                   10                  15

Val Gly Ala Ser Tyr Ala Phe Ala Leu Met Asn Gln Gly Ile Ala Asp
                        20                  25                  30

Glu Ile Val Leu Ile Asp Ala Asn Glu Asn Lys Ala Glu Gly Asp Ala
                    35                  40                  45

Met Asp Phe Asn His Gly Lys Val Phe Ala Pro Lys Pro Ala Asp Ile
                50                  55                  60

Trp His Gly Asp Tyr Asp Asp Cys Arg Asp Ala Asp Leu Val Val Ile
        65                  70                  75                  80

Cys Ala Gly Ala Asn Gln Lys Pro Gly Glu Thr Arg Leu Asp Leu Val
                        85                  90                  95

Asp Lys Asn Ile Ala Ile Phe Arg Ser Ile Val Glu Ser Val Met Ala
                    100                 105                 110

Ser Gly Phe Gln Gly Leu Phe Leu Val Ala Thr Asn Pro Val Asp Ile
                115                 120                 125
```

```
Leu Thr Tyr Ala Thr Trp Lys Phe Ser Gly Leu Pro Gln Glu Arg Val
        130                 135                 140

Ile Gly Ser Gly Thr Ile Leu Asp Thr Ala Arg Phe Arg Phe Leu Leu
145                 150                 155                 160

Gly Asp Tyr Phe Ala Val Ala Pro Thr Asn Val His Ala Tyr Ile Ile
                165                 170                 175

Gly Glu His Gly Asp Thr Glu Leu Pro Val Trp Ser Gln Ala Asp Ile
                180                 185                 190

Gly Gly Val Pro Ile Arg Lys Leu Val Glu Ser Lys Gly Glu Ala
                195                 200                 205

Gln Lys Glu Leu Glu Arg Ile Phe Val Asn Val Arg Asp Ala Ala Tyr
    210                 215                 220

Gln Ile Ile Glu Lys Lys Gly Ala Thr Tyr Tyr Gly Ile Ala Met Gly
225                 230                 235                 240

Leu Ala Arg Val Thr Arg Ala Ile Leu His His Glu Asn Ala Ile Leu
                245                 250                 255

Thr Val Ser Ala Tyr Leu Asp Gly Pro Tyr Gly Glu Arg Asp Val Tyr
                260                 265                 270

Ile Gly Val Pro Ala Val Ile Asn Arg Asn Gly Ile Arg Glu Val Ile
                275                 280                 285

Glu Ile Glu Leu Asp Glu Glu Lys Lys Trp Phe His Arg Ser Ala
    290                 295                 300

Ala Thr Leu Lys Gly Val Leu Ala Arg Tyr Phe Ala Gln
305                 310                 315

<210> SEQ ID NO 14
<211> LENGTH: 310
<212> TYPE: PRT
<213> ORGANISM: Thermus thermophilus

<400> SEQUENCE: 14

Met Lys Val Gly Ile Val Gly Ser Gly Met Val Gly Ser Ala Thr Ala
1               5                   10                  15

Tyr Ala Leu Ala Leu Leu Gly Val Ala Arg Glu Val Leu Val Asp
            20                  25                  30

Leu Asp Arg Lys Leu Ala Gln Ala His Ala Glu Asp Ile Leu His Ala
        35                  40                  45

Thr Pro Phe Ala His Pro Val Trp Val Arg Ala Gly Ser Tyr Gly Asp
    50                  55                  60

Leu Glu Gly Ala Arg Ala Val Leu Ala Ala Gly Val Ala Gln Arg
65                  70                  75                  80

Pro Gly Glu Thr Arg Leu Gln Leu Leu Asp Arg Asn Ala Gln Val Phe
                85                  90                  95

Ala Gln Val Val Pro Arg Val Leu Glu Ala Ala Pro Glu Ala Val Leu
            100                 105                 110

Leu Val Ala Thr Asn Pro Val Asp Val Met Thr Gln Val Ala Tyr Arg
        115                 120                 125

Leu Ser Gly Leu Pro Pro Gly Arg Val Gly Ser Gly Thr Ile Leu
    130                 135                 140

Asp Thr Ala Arg Phe Arg Ala Leu Leu Ala Glu Tyr Leu Arg Val Ala
145                 150                 155                 160

Pro Gln Ser Val His Ala Tyr Val Leu Gly Glu His Gly Asp Ser Glu
                165                 170                 175

Val Leu Val Trp Ser Ser Ala Gln Val Gly Gly Val Pro Leu Leu Glu
            180                 185                 190
```

Phe Ala Glu Ala Arg Gly Arg Ala Leu Ser Pro Glu Asp Arg Ala Arg
            195                 200                 205

Ile Asp Glu Gly Val Arg Arg Ala Ala Tyr Arg Ile Ile Glu Gly Lys
        210                 215                 220

Gly Ala Thr Tyr Tyr Gly Ile Gly Ala Gly Leu Ala Arg Leu Val Arg
225                 230                 235                 240

Ala Ile Leu Thr Asp Glu Lys Gly Val Tyr Thr Val Ser Ala Phe Thr
                245                 250                 255

Pro Glu Val Glu Gly Val Leu Glu Val Ser Leu Ser Leu Pro Arg Ile
            260                 265                 270

Leu Gly Ala Gly Gly Val Glu Gly Thr Val Tyr Pro Ser Leu Ser Pro
        275                 280                 285

Glu Glu Arg Glu Ala Leu Arg Arg Ser Ala Gly Ile Leu Lys Glu Ala
    290                 295                 300

Ala Phe Ala Leu Gly Phe
305                 310

<210> SEQ ID NO 15
<211> LENGTH: 1035
<212> TYPE: DNA
<213> ORGANISM: Thermus thermophilus

<400> SEQUENCE: 15
atgaggtggc gggcggactt cctctcggcc tgggcggagg ccctcttgcg aaaggcggga      60
gcggacgaac cctccgccaa ggcggtggcc tgggccctgg tggaggcgga cctcaggggg     120
gtgggaagcc acgggctttt cgccttcccc gtttacgtgc gccgcctcga ggcgggcctg     180
gtgaaccccc aaccccaccct gcccctggag aacggggccc ccgtggccct cctggacggg     240
gagcacggct tcggaccccg cgtggcccta aggccgtgg aggcggccca agcctcgca      300 aggaggcacg gcctcggggc cgtgggggtg cggcggagca cccacttcgg catggcgggc     360
ctctacgcgg agaagctcgc ccgggagggc ttcgtggcct gggtcaccac caacgccgag     420
cccgacgtgg tgcccttcgg ggggcgggag aaggccttgg gcaccaaccc tctggccttc     480
gccgccccgg cccctcaggg gatcctcgtg ccgacctgg ccacctcgga aagcgccatg     540
ggcaaggtct tcctagcccg ggagaagggg gagcggatcc ccccaagctg gggggtggac     600
cgggagggga gccccacgga cgaccccac cgggtctacg ccctgaggcc cctcggggg      660 cccaaggggt acgccctggc ccttttggtg gaggtgctct cggggggtgct cacggggcg      720 ggggtggccc acggcatcgg ccgcatgtac gacgagtggg accgccccca ggacgtgggc     780
cacttcctcc tggccctgga cccggggcgc ttcgtgggca agaggccttt cctggagcgg     840 atggggccc tttggcaagc cctaaaggcc actccccgg cgccggggca cgaggaggtc      900
ttcctccccg gggagttgga ggccaggagg cgggagcggg ccctggcgga ggggatggcc     960
cttccggagc gggtggtggc ggagcttaag gccttggggg agcgctacgg cgtgccttgg    1020
agggacgatg cttga                                                    1035

<210> SEQ ID NO 16
<211> LENGTH: 1011
<212> TYPE: DNA
<213> ORGANISM: Meiothermus ruber

<400> SEQUENCE: 16
atgcaaggca ttcctgtgca caactgcgc gagcgggtgg agcagattct aataaaccgg       60

-continued

| | |
|---|---|
| ggctttacgc tggagaatgc tctacccatc gcagaatccc tggtgctggc cgagatgcgg | 120 |
| ggggttgcct cgcacggcct gatccgactg cccatctacc tcgagcgcgc ccgactgggt | 180 |
| tcggtaaaac cccaggcccg gcccgtgctg ctggcggatt atccagccct ggccctgctg | 240 |
| gatgccagg atggtcacgg catccccctcc ggcttgaaag cgatggagct ggccattgaa | 300 |
| aaagcccaga aggtgggcct ggccgctgtg ggggtgcggc gctcgagcca ctttggcctg | 360 |
| gcctggtact tcgtgcgcag cgcagtggaa aaggggctgg tcggcgtggc actctccaac | 420 |
| gccgatgcgc tggtggcccc ctggggcgcc cgcagccgct ttctgggcac caaccccctg | 480 |
| gctgtgggca tcccggccat ggaggaaccc cccatcgccc tggacatggc caccagcgag | 540 |
| gccgcccacg gcaaaatttt gctggccaag tccagcggga aaaccatccc cctcaactgg | 600 |
| gccctcgatg cggaggggcg gcccaccgac gaccccgacc gggccctggc cggcgccctg | 660 |
| ctgccttttg gggggcccaa gggatcggcc atcagcctgc tcattgatgt gctgtgcggc | 720 |
| ccactcgtgg gcgctctgat tggccccgag atcgccccgc tctacaccga gcccgaacgg | 780 |
| cccccagggcc tgggccattt ttttatggcc ctgaacccgg gtgttttgg cgacgccgaa | 840 |
| cagtttagaa agcaggtcga cgcgtacatt cgcagggttc gcgcgctgcc tcccgccgaa | 900 |
| aacgtcgatc gggttctact gccaggcgaa cgcgagtggc gcctcgagca aaaagcgcta | 960 |
| caggagggg tgtctctaag cccagaggcc gctaaagcgg tgggccttta a | 1011 |

<210> SEQ ID NO 17
<211> LENGTH: 999
<212> TYPE: DNA
<213> ORGANISM: Meiothermus ruber

<400> SEQUENCE: 17

| | |
|---|---|
| atgagggttc cttatcccgt actcaagcag gcggtctcga gccacttcca gggcctgggg | 60 |
| ctggccccgg atcatgccga ggccttcacc gaggtgatcc tcgaggccga gctcgagggc | 120 |
| aacctggggc acggcctgac ccggattgcc cagtacaccg cccagctaca ggccggtggg | 180 |
| ctcaaccccc ggccgcagat gcgtttggaa cgaaccaaac ccggggttgc agttctgcat | 240 |
| gccgacggcg cacccgggcc ggtggccggg cttttttgcag tgcaggcgct ggccccgatg | 300 |
| gccagggagc agggaagcgc cgccctggcc gtgcgcggcg cggggcattc cggggtgctc | 360 |
| tcggcgtacg tgggccggct ggccaagag ggcctggtag ccctggcctt tgccaacacc | 420 |
| ccccggcca tcgccccggg gccggtgctg ggcaccaacc ccatcgccct gggcgcgccg | 480 |
| gccgagcccc agccggtcat cattgatacc tccatctcgg tggtgcgcg cggcaagatc | 540 |
| atcgccgcgg ctaaaaaggg cgagcccatc ccgccgggct gggcgctcga caaggagggt | 600 |
| cgcccaacca ccgatgccaa ggctgcgctg gaaggctcac tgctgcccat ggcgagggc | 660 |
| aaggggtttg cgctggcagt gctggtggaa attctggccg gggccctggc gggcgacgtg | 720 |
| ctctcgcccg agctgcccct gccctggatg ccccagcgc aggccgccaa gccggggctg | 780 |
| ctgctgctgg cctttgaccc cgccgccttt ggcccgggct acaggggccg gtggcccag | 840 |
| ctcatcgagg ctcttaaagc ggccggaggc cggattcccg tgcgcgccg gccgctta | 900 |
| cgagagaaag cctggcgga aggtctggag gtcaaccaga cgcttcaggc cgaactcggt | 960 |
| acactaggcg tgcatctaca aggaggaggg acaagatga | 999 |

<210> SEQ ID NO 18
<211> LENGTH: 344
<212> TYPE: PRT
<213> ORGANISM: Thermus thermophilus

<400> SEQUENCE: 18

Met Arg Trp Arg Ala Asp Phe Leu Ser Ala Trp Ala Glu Ala Leu Leu
1               5                   10                  15

Arg Lys Ala Gly Ala Asp Glu Pro Ser Ala Lys Ala Val Ala Trp Ala
            20                  25                  30

Leu Val Glu Ala Asp Leu Arg Gly Val Gly Ser His Gly Leu Leu Arg
        35                  40                  45

Leu Pro Val Tyr Val Arg Arg Leu Glu Ala Gly Leu Val Asn Pro Ser
    50                  55                  60

Pro Thr Leu Pro Leu Glu Glu Arg Gly Pro Val Ala Leu Leu Asp Gly
65                  70                  75                  80

Glu His Gly Phe Gly Pro Arg Val Ala Leu Lys Ala Val Glu Ala Ala
                85                  90                  95

Gln Ser Leu Ala Arg Arg His Gly Leu Gly Ala Val Gly Val Arg Arg
            100                 105                 110

Ser Thr His Phe Gly Met Ala Gly Leu Tyr Ala Glu Lys Leu Ala Arg
        115                 120                 125

Glu Gly Phe Val Ala Trp Val Thr Thr Asn Ala Glu Pro Asp Val Val
    130                 135                 140

Pro Phe Gly Gly Arg Glu Lys Ala Leu Gly Thr Asn Pro Leu Ala Phe
145                 150                 155                 160

Ala Ala Pro Ala Pro Gln Gly Ile Leu Val Ala Asp Leu Ala Thr Ser
                165                 170                 175

Glu Ser Ala Met Gly Lys Val Phe Leu Ala Arg Glu Lys Gly Glu Arg
            180                 185                 190

Ile Pro Pro Ser Trp Gly Val Asp Arg Glu Gly Ser Pro Thr Asp Asp
        195                 200                 205

Pro His Arg Val Tyr Ala Leu Arg Pro Leu Gly Gly Pro Lys Gly Tyr
    210                 215                 220

Ala Leu Ala Leu Leu Val Glu Val Leu Ser Gly Val Leu Thr Gly Ala
225                 230                 235                 240

Gly Val Ala His Gly Ile Gly Arg Met Tyr Asp Glu Trp Asp Arg Pro
                245                 250                 255

Gln Asp Val Gly His Phe Leu Leu Ala Leu Asp Pro Gly Arg Phe Val
            260                 265                 270

Gly Lys Glu Ala Phe Leu Glu Arg Met Gly Ala Leu Trp Gln Ala Leu
        275                 280                 285

Lys Ala Thr Pro Pro Ala Pro Gly His Glu Glu Val Phe Leu Pro Gly
    290                 295                 300

Glu Leu Glu Ala Arg Arg Glu Arg Ala Leu Ala Glu Gly Met Ala
305                 310                 315                 320

Leu Pro Glu Arg Val Val Ala Glu Leu Lys Ala Leu Gly Glu Arg Tyr
                325                 330                 335

Gly Val Pro Trp Arg Asp Asp Ala
            340

<210> SEQ ID NO 19
<211> LENGTH: 336
<212> TYPE: PRT
<213> ORGANISM: Meiothermus ruber

<400> SEQUENCE: 19

Met Gln Gly Ile Pro Val Gln Gln Leu Arg Glu Arg Val Glu Gln Ile
1               5                   10                  15

Leu Ile Asn Arg Gly Phe Thr Leu Glu Asn Ala Leu Pro Ile Ala Glu
            20                  25                  30

Ser Leu Val Leu Ala Glu Met Arg Gly Val Ala Ser His Gly Leu Ile
        35                  40                  45

Arg Leu Pro Ile Tyr Leu Glu Arg Ala Arg Leu Gly Ser Val Lys Pro
50                  55                  60

Gln Ala Arg Pro Val Leu Leu Ala Asp Tyr Pro Ala Leu Ala Leu Leu
65                  70                  75                  80

Asp Ala Gln Asp Gly His Gly Ile Pro Ser Gly Leu Lys Ala Met Glu
                85                  90                  95

Leu Ala Ile Glu Lys Ala Gln Lys Val Gly Leu Ala Ala Val Gly Val
            100                 105                 110

Arg Arg Ser Ser His Phe Gly Leu Ala Trp Tyr Phe Val Arg Ser Ala
            115                 120                 125

Val Glu Lys Gly Leu Val Gly Val Ala Leu Ser Asn Ala Asp Ala Leu
    130                 135                 140

Val Ala Pro Trp Gly Ala Arg Ser Arg Phe Leu Gly Thr Asn Pro Leu
145                 150                 155                 160

Ala Val Gly Ile Pro Ala Met Glu Glu Pro Ile Ala Leu Asp Met
                165                 170                 175

Ala Thr Ser Glu Ala Ala His Gly Lys Ile Leu Leu Ala Lys Ser Ser
            180                 185                 190

Gly Lys Thr Ile Pro Leu Asn Trp Ala Leu Asp Ala Glu Gly Arg Pro
            195                 200                 205

Thr Asp Asp Pro Asp Arg Ala Leu Ala Gly Ala Leu Leu Pro Phe Gly
    210                 215                 220

Gly Pro Lys Gly Ser Ala Ile Ser Leu Leu Ile Asp Val Leu Cys Gly
225                 230                 235                 240

Pro Leu Val Gly Ala Leu Ile Gly Pro Glu Ile Ala Pro Leu Tyr Thr
                245                 250                 255

Glu Pro Glu Arg Pro Gln Gly Leu Gly His Phe Met Ala Leu Asn
            260                 265                 270

Pro Gly Val Phe Gly Asp Ala Glu Gln Phe Arg Lys Gln Val Asp Ala
            275                 280                 285

Tyr Ile Arg Arg Val Arg Ala Leu Pro Pro Ala Glu Asn Val Asp Arg
    290                 295                 300

Val Leu Leu Pro Gly Glu Arg Glu Trp Arg Leu Glu Gln Lys Ala Leu
305                 310                 315                 320

Gln Glu Gly Val Ser Leu Ser Pro Glu Ala Ala Lys Ala Val Gly Leu
                325                 330                 335

<210> SEQ ID NO 20
<211> LENGTH: 332
<212> TYPE: PRT
<213> ORGANISM: Meiothermus ruber

<400> SEQUENCE: 20

Met Arg Val Pro Tyr Pro Val Leu Lys Gln Ala Val Ser Ser His Phe
1               5                   10                  15

Gln Gly Leu Gly Leu Ala Pro Asp His Ala Glu Ala Phe Thr Glu Val
            20                  25                  30

Ile Leu Glu Ala Glu Leu Glu Gly Asn Leu Gly His Gly Leu Thr Arg
        35                  40                  45

Ile Ala Gln Tyr Thr Ala Gln Leu Gln Ala Gly Gly Leu Asn Pro Arg

```
            50                  55                  60
Pro Gln Met Arg Leu Glu Arg Thr Lys Pro Gly Val Ala Val Leu His
 65                  70                  75                  80

Ala Asp Gly Ala Pro Gly Pro Val Ala Gly Leu Phe Ala Val Gln Ala
                 85                  90                  95

Leu Ala Pro Met Ala Arg Glu Gln Gly Ser Ala Ala Leu Ala Val Arg
            100                 105                 110

Gly Ala Gly His Ser Gly Val Leu Ser Ala Tyr Val Gly Arg Leu Ala
        115                 120                 125

Gln Glu Gly Leu Val Ala Leu Ala Phe Ala Asn Thr Pro Pro Ala Ile
    130                 135                 140

Ala Pro Gly Pro Val Leu Gly Thr Asn Pro Ile Ala Leu Gly Ala Pro
145                 150                 155                 160

Ala Glu Pro Gln Pro Val Ile Ile Asp Thr Ser Ile Ser Val Val Ala
                165                 170                 175

Arg Gly Lys Ile Ile Ala Ala Lys Lys Gly Glu Pro Ile Pro Pro
            180                 185                 190

Gly Trp Ala Leu Asp Lys Glu Gly Arg Pro Thr Thr Asp Ala Lys Ala
        195                 200                 205

Ala Leu Glu Gly Ser Leu Leu Pro Ile Gly Glu Gly Lys Gly Phe Ala
    210                 215                 220

Leu Ala Val Leu Val Glu Ile Leu Ala Gly Ala Leu Ala Gly Asp Val
225                 230                 235                 240

Leu Ser Pro Glu Leu Pro Leu Pro Trp Met Pro Ala Gln Ala Ala
                245                 250                 255

Lys Pro Gly Leu Leu Leu Ala Phe Asp Pro Ala Ala Phe Gly Pro
            260                 265                 270

Gly Tyr Arg Gly Arg Val Ala Gln Leu Ile Glu Ala Leu Lys Ala Ala
        275                 280                 285

Gly Gly Arg Ile Pro Gly Ala Arg Arg Ala Ala Leu Arg Glu Lys Ala
    290                 295                 300

Leu Ala Glu Gly Leu Glu Val Asn Gln Thr Leu Gln Ala Glu Leu Gly
305                 310                 315                 320

Thr Leu Gly Val His Leu Gln Gly Gly Gly Thr Arg
                325                 330

<210> SEQ ID NO 21
<211> LENGTH: 1674
<212> TYPE: DNA
<213> ORGANISM: Geobacillus kaustophilus

<400> SEQUENCE: 21
atgtggaagc aagattttac accaatcgcc gaccagcttt ggttatcggc gattgtcgca    60
ctcattccga ttttatattt cttttgggcg ttggccgtca agcggatgaa agggcatgtt   120
gcggggctga cgacgttgct gcttgctgtt gtgttggctg taatcgctta cagaatgccg   180
gctggaaaag cggttatgtc agtgacgcaa ggcgcggtgt acggattgtt gccgatcggc   240
tggatcatca tcacctctgt cttttttatac aagctgacgg tgaaaacagg ccactttgac   300
attatccgca attcggttgt ctcgctcacc gaagaccgcc ggctgcaagc gttgctgatt   360 gcctttcgt ttggcgcctt tttggaaggg gcagctgggt tggcgcgcc agtggcgatt   420 tcagcggcgc ttcttgcggg gttgggggtt aacccgctgt atgccgcggg catttgcttg   480
atcgccaaca cagcgccagt ggcattcggg gcggtcggga ttccaatcat ttcgatggaa   540
```

```
ggaccgactg gcgtgccggc gatggaaatc tcaaaaatgg ttgggcggca gttgccgttt    600
ttatcagtgt tcatcccgtt ctatctcgtg ctcattatgg ccgggtggaa aaagacgatg    660
gaagtgttgc cggccattat cgtttccggt gtttcgtttg cgctgacgca atatttcacc    720
tcgaactttt taggaccgga gctgccggac attttgtcct cgctcgtttc gatcgtcgcg    780
ttggctgtct ttttgaaata ttggaagccg aaaagcacat tccgctttgc aacggagtcg    840
gaagtggcgg ccgctgggca agttgctcgc gcgacgcaac gcggcgggga agtattccgc    900
gcttggtcgc cgtttctcgt gctgacggct ttgatctcgc tgtggggcat cccgcaagtg    960
aaggcggcgc tcaccggcca ttatgaaggg acaaacggct tgttgaagtt ggtcaacgct   1020
atcggcgtcc acttgacgtt tatgccgcct gtgccgggc tcaacaacca aattttgaac   1080
ccaagtggcc agccgatcgc tgcggtgtat aagcttgagc tgctcggcgc ggctgggacg   1140
gcgattttgc tggcggcggt cgtcacaaag ttcatcatcg gcatctcgtg gaaagagtgg   1200
gcgcgtacgt ttgtggaaac gcttaacgaa ttgaaattcc cgatcatcac gatcgcttcg   1260
gttgtcggct ttgcctatat cgccaactcg tcaggcatga gcacgacgct tggaatggcg   1320
ttggccaaaa caggcccgtt gttcccgttc ttctcgccga ttttaggatg gctcggcgtg   1380
tttatcaccg gttccgacac gtcgtcgaac ttgttgttcg gcaacctgca aaaagtgacg   1440
gcgacatcga ttggcatgga tccggtgctg gcgttggcgg ccaactcatc aggcggcgtc   1500
gtcgggaaaa tgatttcgcc gcaatcgatc gctgtcgcct gtgcggccgt cggtttgacc   1560
ggcaaagaat ccgacttgtt ccgcttcacg atcaaacata gcgtgttctt aatcatcttg   1620
attggcgttc tcgtttactt gcaatcgacg gtattgtcgt ggatgattcc ataa         1674
```

<210> SEQ ID NO 22
<211> LENGTH: 557
<212> TYPE: PRT
<213> ORGANISM: Geobacillus kaustophilus
<400> SEQUENCE: 22

Met Trp Lys Gln Asp Phe Thr Pro Ile Ala Asp Gln Leu Trp Leu Ser
1               5                   10                  15

Ala Ile Val Ala Leu Ile Pro Ile Leu Tyr Phe Phe Trp Ala Leu Ala
            20                  25                  30

Val Lys Arg Met Lys Gly His Val Ala Gly Leu Thr Thr Leu Leu Leu
        35                  40                  45

Ala Val Val Leu Ala Val Ile Ala Tyr Arg Met Pro Ala Gly Lys Ala
    50                  55                  60

Val Met Ser Val Thr Gln Gly Ala Val Tyr Gly Leu Leu Pro Ile Gly
65                  70                  75                  80

Trp Ile Ile Ile Thr Ser Val Phe Leu Tyr Lys Leu Thr Val Lys Thr
                85                  90                  95

Gly His Phe Asp Ile Ile Arg Asn Ser Val Val Ser Leu Thr Glu Asp
            100                 105                 110

Arg Arg Leu Gln Ala Leu Leu Ile Ala Phe Ser Phe Gly Ala Phe Leu
        115                 120                 125

Glu Gly Ala Ala Gly Phe Gly Ala Pro Val Ala Ile Ser Ala Ala Leu
    130                 135                 140

Leu Ala Gly Leu Gly Phe Asn Pro Leu Tyr Ala Ala Gly Ile Cys Leu
145                 150                 155                 160

Ile Ala Asn Thr Ala Pro Val Ala Phe Gly Ala Val Gly Ile Pro Ile
                165                 170                 175

```
Ile Ser Met Glu Gly Pro Thr Gly Val Pro Ala Met Glu Ile Ser Lys
                180                 185                 190

Met Val Gly Arg Gln Leu Pro Phe Leu Ser Val Phe Ile Pro Phe Tyr
            195                 200                 205

Leu Val Leu Ile Met Ala Gly Trp Lys Lys Thr Met Glu Val Leu Pro
        210                 215                 220

Ala Ile Ile Val Ser Gly Val Ser Phe Ala Leu Thr Gln Tyr Phe Thr
225                 230                 235                 240

Ser Asn Phe Leu Gly Pro Glu Leu Pro Asp Ile Leu Ser Ser Leu Val
                245                 250                 255

Ser Ile Val Ala Leu Ala Val Phe Leu Lys Tyr Trp Lys Pro Lys Ser
            260                 265                 270

Thr Phe Arg Phe Ala Thr Glu Ser Glu Val Ala Ala Gly Gln Val
        275                 280                 285

Ala Arg Ala Thr Gln Arg Gly Gly Glu Val Phe Arg Ala Trp Ser Pro
        290                 295                 300

Phe Leu Val Leu Thr Ala Leu Ile Ser Leu Trp Gly Ile Pro Gln Val
305                 310                 315                 320

Lys Ala Ala Leu Thr Gly His Tyr Glu Gly Thr Asn Gly Leu Leu Lys
                325                 330                 335

Leu Val Asn Ala Ile Gly Val His Leu Thr Phe Met Pro Pro Val Pro
            340                 345                 350

Gly Leu Asn Asn Gln Ile Leu Asn Pro Ser Gly Gln Pro Ile Ala Ala
        355                 360                 365

Val Tyr Lys Leu Glu Leu Leu Gly Ala Ala Gly Thr Ala Ile Leu Leu
370                 375                 380

Ala Ala Val Val Thr Lys Phe Ile Ile Gly Ile Ser Trp Lys Glu Trp
385                 390                 395                 400

Ala Arg Thr Phe Val Glu Thr Leu Asn Glu Leu Lys Phe Pro Ile Ile
                405                 410                 415

Thr Ile Ala Ser Val Val Gly Phe Ala Tyr Ile Ala Asn Ser Ser Gly
            420                 425                 430

Met Ser Thr Thr Leu Gly Met Ala Leu Ala Lys Thr Gly Pro Leu Phe
        435                 440                 445

Pro Phe Phe Ser Pro Ile Leu Gly Trp Leu Gly Val Phe Ile Thr Gly
450                 455                 460

Ser Asp Thr Ser Ser Asn Leu Leu Phe Gly Asn Leu Gln Lys Val Thr
465                 470                 475                 480

Ala Thr Ser Ile Gly Met Asp Pro Val Leu Ala Leu Ala Ala Asn Ser
                485                 490                 495

Ser Gly Gly Val Val Gly Lys Met Ile Ser Pro Gln Ser Ile Ala Val
            500                 505                 510

Ala Cys Ala Ala Val Gly Leu Thr Gly Lys Glu Ser Asp Leu Phe Arg
        515                 520                 525

Phe Thr Ile Lys His Ser Val Phe Leu Ile Leu Ile Gly Val Leu
530                 535                 540

Val Tyr Leu Gln Ser Thr Val Leu Ser Trp Met Ile Pro
545                 550                 555
```

<210> SEQ ID NO 23
<211> LENGTH: 35
<212> TYPE: DNA
<213> ORGANISM: Artificial sequence
<220> FEATURE:
<223> OTHER INFORMATION: PCR primer

```
<400> SEQUENCE: 23
atacgcgtcc tccgatgcgt cgtaagggaa acgtc                        35

<210> SEQ ID NO 24
<211> LENGTH: 35
<212> TYPE: DNA
<213> ORGANISM: Artificial sequence
<220> FEATURE:
<223> OTHER INFORMATION: PCR primer

<400> SEQUENCE: 24
atagtcgact tatttcttgc ccgcagcggc gcccg                        35

<210> SEQ ID NO 25
<211> LENGTH: 35
<212> TYPE: DNA
<213> ORGANISM: Artificial sequence
<220> FEATURE:
<223> OTHER INFORMATION: PCR primer

<400> SEQUENCE: 25
atactcgagg agatgacgtt ggaggggcaa ggtcg                        35

<210> SEQ ID NO 26
<211> LENGTH: 35
<212> TYPE: DNA
<213> ORGANISM: Artificial sequence
<220> FEATURE:
<223> OTHER INFORMATION: PCR primer

<400> SEQUENCE: 26
atacgcgtct attcctttgc cctcggacga gtgct                        35

<210> SEQ ID NO 27
<211> LENGTH: 35
<212> TYPE: DNA
<213> ORGANISM: Artificial sequence
<220> FEATURE:
<223> OTHER INFORMATION: PCR primer

<400> SEQUENCE: 27
cgcgaattca tggctaccca accccgcgtc ggtct                        35

<210> SEQ ID NO 28
<211> LENGTH: 35
<212> TYPE: DNA
<213> ORGANISM: Artificial sequence
<220> FEATURE:
<223> OTHER INFORMATION: PCR primer

<400> SEQUENCE: 28
cgcacgcgtt ggagtgcggc tggtcatcgg gtgac                        35

<210> SEQ ID NO 29
<211> LENGTH: 35
<212> TYPE: DNA
<213> ORGANISM: Artificial sequence
<220> FEATURE:
<223> OTHER INFORMATION: PCR primer

<400> SEQUENCE: 29
gcacgcgtct gcagaacgga ggcgagcgat gaacg                        35

<210> SEQ ID NO 30
```

```
<211> LENGTH: 35
<212> TYPE: DNA
<213> ORGANISM: Artificial sequence
<220> FEATURE:
<223> OTHER INFORMATION: PCR primer

<400> SEQUENCE: 30
cgcgcatgct cagggatca agaagacgtg caccc                              35

<210> SEQ ID NO 31
<211> LENGTH: 35
<212> TYPE: DNA
<213> ORGANISM: Artificial sequence
<220> FEATURE:
<223> OTHER INFORMATION: PCR primer

<400> SEQUENCE: 31
cgcgaattca tggctaccca accccgcgtc ggtct                             35

<210> SEQ ID NO 32
<211> LENGTH: 35
<212> TYPE: DNA
<213> ORGANISM: Artificial sequence
<220> FEATURE:
<223> OTHER INFORMATION: PCR primer

<400> SEQUENCE: 32
cgcgcatgct cagggatca agaagacgtg caccc                              35

<210> SEQ ID NO 33
<211> LENGTH: 12
<212> TYPE: DNA
<213> ORGANISM: Artificial sequence
<220> FEATURE:
<223> OTHER INFORMATION: Nucleotide sequence to replace internal
      sequence of HPTL_1695 gene

<400> SEQUENCE: 33
acgcgtctgc ag                                                      12

<210> SEQ ID NO 34
<211> LENGTH: 4
<212> TYPE: PRT
<213> ORGANISM: Artificial sequence
<220> FEATURE:
<223> OTHER INFORMATION: Amino acid sequence to replace internal
      sequence of polypeptide coded by HPTL_1695 gene

<400> SEQUENCE: 34

Thr Arg Leu Gln
1

<210> SEQ ID NO 35
<211> LENGTH: 35
<212> TYPE: DNA
<213> ORGANISM: Artificial sequence
<220> FEATURE:
<223> OTHER INFORMATION: PCR primer

<400> SEQUENCE: 35
cgtggccaac taggcccagc cagatactcc cgatc                             35

<210> SEQ ID NO 36
<211> LENGTH: 35
<212> TYPE: DNA
<213> ORGANISM: Artificial sequence
<220> FEATURE:
```

<223> OTHER INFORMATION: PCR primer

<400> SEQUENCE: 36
tgaggcctca ttggccggag cgcaacccac tcact                          35

<210> SEQ ID NO 37
<211> LENGTH: 35
<212> TYPE: DNA
<213> ORGANISM: Artificial sequence
<220> FEATURE:
<223> OTHER INFORMATION: PCR primer

<400> SEQUENCE: 37
ctgggcctag ttggccacgt agaaagccag tccgc                          35

<210> SEQ ID NO 38
<211> LENGTH: 35
<212> TYPE: DNA
<213> ORGANISM: Artificial sequence
<220> FEATURE:
<223> OTHER INFORMATION: PCR primer

<400> SEQUENCE: 38
tccggccaat gaggcctcag aagaactcgt caaga                          35

<210> SEQ ID NO 39
<211> LENGTH: 83
<212> TYPE: DNA
<213> ORGANISM: Artificial sequence
<220> FEATURE:
<223> OTHER INFORMATION: PCR primer

<400> SEQUENCE: 39
gcattaatcc ttggactcct gttgatagat ccagtaatga cctcagaact ccatctggat    60
ttgttcagaa cgctcggttg ccg                                           83

<210> SEQ ID NO 40
<211> LENGTH: 83
<212> TYPE: DNA
<213> ORGANISM: Artificial sequence
<220> FEATURE:
<223> OTHER INFORMATION: PCR primer

<400> SEQUENCE: 40
caccgtgcag tcgatggatc tggattctca ccaataaaaa acgcccggcg gcaaccgagc    60
gttctgaaca aatccagatg gag                                           83

<210> SEQ ID NO 41
<211> LENGTH: 50
<212> TYPE: DNA
<213> ORGANISM: Artificial sequence
<220> FEATURE:
<223> OTHER INFORMATION: PCR primer

<400> SEQUENCE: 41
ttattggtga gaatccagat ccatcgactg cacggtgcac caatgcttct              50

<210> SEQ ID NO 42
<211> LENGTH: 70
<212> TYPE: DNA
<213> ORGANISM: Artificial sequence
<220> FEATURE:
<223> OTHER INFORMATION: PCR primer

<400> SEQUENCE: 42

```
gcaagcttgg agtgatcatc gtatgcatat gcgtttctcc tccagatccc tgtttcctgt    60
gtgaaattgt                                                            70

<210> SEQ ID NO 43
<211> LENGTH: 35
<212> TYPE: DNA
<213> ORGANISM: Artificial sequence
<220> FEATURE:
<223> OTHER INFORMATION: PCR primer

<400> SEQUENCE: 43
ctcgaattca ctggccgtcg ttttacaacg tcgtg                                35

<210> SEQ ID NO 44
<211> LENGTH: 35
<212> TYPE: DNA
<213> ORGANISM: Artificial sequence
<220> FEATURE:
<223> OTHER INFORMATION: PCR primer

<400> SEQUENCE: 44
cgcaattgag tttgtagaaa cgcaaaaagg ccatc                                35

<210> SEQ ID NO 45
<211> LENGTH: 35
<212> TYPE: DNA
<213> ORGANISM: Artificial sequence
<220> FEATURE:
<223> OTHER INFORMATION: PCR primer

<400> SEQUENCE: 45
ttacatatga acaacaagg catgaatcga gtagc                                 35

<210> SEQ ID NO 46
<211> LENGTH: 35
<212> TYPE: DNA
<213> ORGANISM: Artificial sequence
<220> FEATURE:
<223> OTHER INFORMATION: PCR primer

<400> SEQUENCE: 46
ttagaattct tattttacat catcaaaata acggg                                35

<210> SEQ ID NO 47
<211> LENGTH: 35
<212> TYPE: DNA
<213> ORGANISM: Artificial sequence
<220> FEATURE:
<223> OTHER INFORMATION: PCR primer

<400> SEQUENCE: 47
ttacatatga aaacgggag aggaaatcgg gtagc                                 35

<210> SEQ ID NO 48
<211> LENGTH: 35
<212> TYPE: DNA
<213> ORGANISM: Artificial sequence
<220> FEATURE:
<223> OTHER INFORMATION: PCR primer

<400> SEQUENCE: 48
ttagaattct tactgagcaa aatagcgcgc caata                                35

<210> SEQ ID NO 49
```

-continued

<211> LENGTH: 35
<212> TYPE: DNA
<213> ORGANISM: Artificial sequence
<220> FEATURE:
<223> OTHER INFORMATION: PCR primer

<400> SEQUENCE: 49
ttacatatga aggtcggcat cgtgggaagc ggcat         35

<210> SEQ ID NO 50
<211> LENGTH: 35
<212> TYPE: DNA
<213> ORGANISM: Artificial sequence
<220> FEATURE:
<223> OTHER INFORMATION: PCR pimer

<400> SEQUENCE: 50
ttagaattcc taaaacccca gggcgaaggc cgcct         35

<210> SEQ ID NO 51
<211> LENGTH: 35
<212> TYPE: DNA
<213> ORGANISM: Artificial sequence
<220> FEATURE:
<223> OTHER INFORMATION: PCR primer

<400> SEQUENCE: 51
ttacatatga ggtggcgggc ggacttcctc tcggc         35

<210> SEQ ID NO 52
<211> LENGTH: 35
<212> TYPE: DNA
<213> ORGANISM: Artificial sequence
<220> FEATURE:
<223> OTHER INFORMATION: PCR primer

<400> SEQUENCE: 52
ttagaattct caagcatcgt ccctccaagg cacgc         35

<210> SEQ ID NO 53
<211> LENGTH: 35
<212> TYPE: DNA
<213> ORGANISM: Artificial sequence
<220> FEATURE:
<223> OTHER INFORMATION: PCR primer

<400> SEQUENCE: 53
ttacatatgc aaggcattcc tgtgcaacaa ctgcg         35

<210> SEQ ID NO 54
<211> LENGTH: 35
<212> TYPE: DNA
<213> ORGANISM: Artificial sequence
<220> FEATURE:
<223> OTHER INFORMATION: PCR primer

<400> SEQUENCE: 54
ttagaattct taaaggccca ccgctttagc ggcct         35

<210> SEQ ID NO 55
<211> LENGTH: 35
<212> TYPE: DNA
<213> ORGANISM: Artificial sequence
<220> FEATURE:
<223> OTHER INFORMATION: PCR primer

<400> SEQUENCE: 55

```
ttacatatga gggttcctta tcccgtactc aagca                                35

<210> SEQ ID NO 56
<211> LENGTH: 35
<212> TYPE: DNA
<213> ORGANISM: Artificial sequence
<220> FEATURE:
<223> OTHER INFORMATION: PCR primer

<400> SEQUENCE: 56
tttgaattct catcttgtcc ctcctccttg tagat                                35

<210> SEQ ID NO 57
<211> LENGTH: 35
<212> TYPE: DNA
<213> ORGANISM: Artificial sequence
<220> FEATURE:
<223> OTHER INFORMATION: PCR primer

<400> SEQUENCE: 57
cggcaattgc gggcacaaag gggaggagaa aaccg                                35

<210> SEQ ID NO 58
<211> LENGTH: 35
<212> TYPE: DNA
<213> ORGANISM: Artificial sequence
<220> FEATURE:
<223> OTHER INFORMATION: PCR primer

<400> SEQUENCE: 58
cggcaattgt tatggaatca tccacgacaa taccg                                35

<210> SEQ ID NO 59
<211> LENGTH: 35
<212> TYPE: DNA
<213> ORGANISM: Artificial sequence
<220> FEATURE:
<223> OTHER INFORMATION: PCR primer

<400> SEQUENCE: 59
ggctcgtata atgtgtggaa ttgtgagcgg ataac                                35

<210> SEQ ID NO 60
<211> LENGTH: 35
<212> TYPE: DNA
<213> ORGANISM: Artificial sequence
<220> FEATURE:
<223> OTHER INFORMATION: PCR primer

<400> SEQUENCE: 60
cggcaattgt tatggaatca tccacgacaa taccg                                35
```